United States Patent
Abe et al.

(10) Patent No.: US 7,405,667 B2
(45) Date of Patent: Jul. 29, 2008

(54) APPARATUS FOR DETERMINING TYPE OF LIQUID IN A CONTAINER AND METHOD FOR CONTROLLING THE APPARATUS

(75) Inventors: Takeshi Abe, Tokyo (JP); Yasuhiko Shinozawa, Tokyo (JP); Yoshinobu Miyagi, Tokyo (JP); Kouichiro Yamada, Tokyo (JP); Tomohide Machida, Tokyo (JP)

(73) Assignee: Tokyo Gas Co., Ltd, Tokyo (JP)

( * ) Notice: Subject to any disclaimer, the term of this patent is extended or adjusted under 35 U.S.C. 154(b) by 219 days.

(21) Appl. No.: 10/584,331

(22) PCT Filed: Dec. 22, 2004

(86) PCT No.: PCT/JP2004/019245

§ 371 (c)(1),
(2), (4) Date: Jun. 26, 2006

(87) PCT Pub. No.: WO2005/064324

PCT Pub. Date: Jul. 14, 2005

(65) Prior Publication Data

US 2007/0146149 A1 Jun. 28, 2007

(30) Foreign Application Priority Data

Dec. 26, 2003 (JP) .............................. 2003-432833
Mar. 16, 2004 (JP) .............................. 2004-074198

(51) Int. Cl.
*G08B 17/00* (2006.01)
(52) U.S. Cl. ..................... 340/589; 340/622; 340/584; 73/61.76; 702/136
(58) Field of Classification Search ................. 340/540, 340/584, 588–589, 622; 73/61.76–61.77, 73/75, 77; 702/25, 50, 136
See application file for complete search history.

(56) References Cited

FOREIGN PATENT DOCUMENTS

JP 10-325815 A 12/1998

(Continued)

OTHER PUBLICATIONS

International Search Report mailed Apr. 19, 2005 of International Application PCT/JP2004/019245.

(Continued)

*Primary Examiner*—Davetta W. Goins
*Assistant Examiner*—Hongmin Fan
(74) *Attorney, Agent, or Firm*—Westerman, Hattori, Daniels & Adrian, LLP.

(57) ABSTRACT

A technique for quickly determining the type of liquid in a container externally regardless of the material of the container, preferably contactlessly. A halogen heater 102 and an infrared thermopile 103 are disposed outside an electrically conductive container 101 made of aluminum, for example. The surface temperature of the container 101 is measured when the halogen heater 102 is off, followed by the turning-on of the halogen heater 102 for two seconds, for example. The surface temperature of the container 101 is then measured, and a difference from the previous result of measurement is calculated. If the difference is smaller than a threshold value, the liquid in the container is determined to be a safe liquid consisting primarily of water, and a blue lamp is activated. If the difference is greater than the threshold value, the liquid in the container cannot be determined to be a safe liquid consisting primarily of water, and a red lamp is activated, indicating abnormality.

34 Claims, 18 Drawing Sheets

FOREIGN PATENT DOCUMENTS

| | | |
|---|---|---|
| JP | 11-51953 A | 2/1999 |
| JP | 2000-186815 A | 7/2000 |
| JP | 2002-214020 A | 7/2002 |
| JP | 2002-277416 A | 9/2002 |
| WO | WO 00/65343 A1 | 11/2000 |

OTHER PUBLICATIONS

Translation of International Preliminary Report on Patentability mailed Aug. 31, 2006.

APPARATUS FOR DETERMINING TYPE OF LIQUID IN A CONTAINER AND METHOD FOR CONTROLLING THE APPARATUS

TECHNICAL FIELD

The present invention relates to an apparatus and method for determining the type of liquid in a container, and particularly to a technique for determining whether a liquid in a container is a liquid consisting primarily of water and is not dangerous.

BACKGROUND ART

Passenger transporting institutions, such as airlines, railroads, and bus companies, have the duty to transport passengers safely. In particular, accidents involving aircraft can lead to disasters and a very high level of safety is required. Thus, airplane passengers are subjected to various tests, such as baggage inspection using X-ray imaging devices, body check through frisking or using metal detectors, and, if necessary, interrogation, so as to pick out passengers with malicious intent and prevent them from boarding the airplane. However, in view of the large number of passengers and the convenience for them, it is difficult to subject all the passengers to strict inspections over a long time or to interrogations. Meanwhile, passengers with malicious intent (such as terrorists) try to slip through these inspections and bring dangerous objects on board. While there would be no problem as long as such dangerous objects can be detected by the current baggage inspection and the like, there are some objects that are difficult to detect using metal detectors or X-ray imaging devices, such as gasoline and other combustible liquids. Gasoline and other dangerous liquids are easy to obtain on the market. If such a dangerous liquid is contained in a commercially available beverage container (such as a PET bottle), for example, it becomes more difficult to distinguish it from authentic beverages, and someone with sinister intent could readily adopt such technique. Thus, it is necessary to devise and prepare countermeasures against such dangerous acts.

In order to distinguish a dangerous liquid such as gasoline from a beverage that typically consists primarily of water, the liquid could be subjected to a sensory test, such as smelling, or other various methods. However, in the baggage inspection before boarding an airplane, time is of utmost concern and the inspection should be completed as quickly as possible. In response to such needs, the inventors had developed a method for determining the type of liquid in containers made of insulating (dielectric) material, such as PET bottles, based on the difference in dielectric constant that depends on the type of the liquid. The inventions associated with such technique are described in the specification attached to JP Patent Application No. 2003-198046 or 2003-385627 filed by the same applicants as the present application.

Besides the aforementioned method for determining the type of a liquid based on the difference in dielectric constant that depends on the type of liquid, a method is conceivable that takes advantage of the difference in thermal characteristics that depend on the type of liquid. For example, Patent Document 1 discloses a technique involving a heat supply means and a temperature-change measuring means that are disposed inside the fuel tank such as the gas tank of an automobile. In this technique, the nature of the fuel (such as its boiling point and T50 value) inside the tank is detected based on the behavior of heat transmitted to heat conducting members on the side of the wall surface of the tank and on the side of the fuel. Patent Document 2 discloses a technique whereby, in order to detect the introduction of water and the like into a petroleum tank or oil delivery channels, an indirectly heated flow detector is used as a fluid distinguishing device. It is well-known that an indirectly heated flowmeter is a current meter comprised of a heating element and a flow rate detecting element (temperature sensor) that are disposed within the fluid, and that it utilizes the property that the temperature of the flow rate detecting element varies depending on the rate of the fluid. In the technique disclosed in Patent Document 2, the fact that the initial output at rate zero of the indirectly heated flowmeter varies depending on the thermal characteristics of the fluid that is in contact therewith is used for the identification of the fluid. Furthermore, Patent Document 3 discloses a technique involving a level measuring device that utilizes a measurement module equipped with a heating means for heating the outer surface of a container and a temperature sensor disposed in the vicinity of the heating means. In this level measuring device, a plurality of measurement modules are arranged outside the container in a row in a biased manner, and the device aims to detect between which measurement modules the fluid level is at based on the difference in behavior of the heat in the container outer wall when there is liquid in the container and when there is not. These techniques disclosed by Patent Documents 1 to 3 all attempt to distinguish the type of liquid (or the presence or absence thereof) based on the thermal characteristics of the liquid (including when there is no liquid).

Patent Document 1: JP Patent Publication (Kokai) No. 10-325815 A (1998)

Patent Document 2: JP Patent Publication (Kokai) No. 2000-186815 A

Patent Document 3: JP Patent Publication (Kokai) No. 2002-214020 A

DISCLOSURE OF THE INVENTION

Problem to be Solved by the Invention

As mentioned above, the inventors had developed an apparatus and method for distinguishing the type of a liquid in a container based on the difference in dielectric constant depending on the type of the liquid, as an inspection apparatus suitable for the determination of whether or not a liquid about to be brought on board an airplane or the like is dangerous. However, as will be seen from the principle of measurement, the technique is only applicable when the container is made of insulating (dielectric) material. Beverage containers that can be brought on board are not limited to PET and glass bottles and other insulators, but there are conductive metal containers such as aluminum cans. Therefore, there is a need for a quick and contactless inspection method capable of handling these conductive metal containers as well as PET bottles and the like.

For distinguishing the type of liquid in a conductive container, the techniques according to Patent Documents 1 to 3 can be used. However, the sensors disclosed in Patent Documents 1 and 2 are both disposed within the container and are not suitable when speed is of concern, such as during the baggage inspection prior to boarding an airplane as mentioned above. In addition, the techniques of Patent Documents 1 and 2 require that the sensor be in contact with the liquid inside the container, which requires a sealed beverage to be opened in a kind of destructive inspection. Having the sensor come into contact with the beverage is not preferable from the hygienic point of view as well. Thus, the aforementioned techniques cannot be adopted for baggage inspection and the like. In view of the application to airplane baggage inspection, a technique is indispensable that allows the type of liquid inside a container to be distinguished from the outside. The technique according to Patent Document 3 is actually capable of measuring the nature of liquid (whether or not there is liquid) from the outside of the container. However, it is only capable of detecting the presence or absence of liquid and not the type of liquid.

In a method capable of quickly determining the type of liquid in a container made of a conductive material, such as aluminum, without opening it, an infrared heat source such as a halogen lamp is used for contactless measurement. The inventors, however, are aware of several points to be improved upon when this technique is adopted. Namely, the heating of the container outer wall with the infrared heat source such as a halogen lamp is associated with the problem of different heated conditions depending on the nature of the outer wall of the container, such as the shape of the container outer wall or the type of paint applied thereto. Thus, in the system whereby the temperature near a heated site is measured in a contactless manner, errors in the measured value may increase due to the influence of the shape or the like of the container outer wall. Further, when a halogen lamp is used, the life of the apparatus is limited by the life of the halogen lamp in contradiction to the need to extend the life of the apparatus. In addition, there are other needs, such as to reduce the size of the heating and temperature measuring means and to design such means adapted for mass production.

It is an object of the invention to provide a technique for quickly distinguishing the type of liquid in a container regardless of the material of the container and from the outside the container, preferably in a contactless manner. It is another object of the invention to provide a liquid determination technique for quickly determining the type of liquid in a container regardless of the material of the container and from the outside thereof, whereby the container outer wall are heated stably and the temperature near a heated site can be stably measured. Yet another object of the invention is to extend the life of a relevant apparatus. Still another object of the invention is to achieve a reduction in size of a heating unit and a temperature measuring unit, and to provide an apparatus suitable for mass production.

Means For Solving the Problem

The inventions disclosed in the present specification are as follows, which are referred to as invention 1, invention 2, and so on in order to distinguish one from another. The numbering is provided only for indexing purposes and for the sake of convenience, and it does not indicate the relative scopes of the inventions or their orders. An apparatus for determining the type of liquid in a container according to invention 1 includes a heat source disposed outside a container, a temperature sensor disposed near the heat source for converting the temperature of the outer wall of the container into a voltage or current, a notification means capable of issuing an alert indicating that the content of the container is dangerous, and a control determination circuit whereby the supply of power to the heat source is controlled, and whereby a difference between the value of an output of the temperature sensor at time t1 which is before or when power is supplied to the heat source, and the value of an output of the temperature sensor at time t1+t2 which is when a predetermined time t2 has passed since the time t1, is compared with a predetermined threshold value, and whereby an alert signal is outputted to the notification means.

In the apparatus for determining the type of liquid in a container according to invention 1, heat is supplied to a localized portion of the container wall for a certain time, and then the temperature change in the container wall near where heat was supplied is measured. A model of how the heat supplied to the container wall is diffused consists of two paths, namely, one in which the heat is conducted in the container (container material) and the other in which the heat is conducted to the liquid in the container. Assuming that the area of the portion where heat is supplied is sufficiently small relative to the total area of the container wall, and that a region of concern (the site where temperature is measured) is sufficiently close to the heat-supplied portion, the container wall to which heat is supplied can be considered to be a flat plate extending to infinity. Thus, the heat supplied at a spot can be considered to diffuse radially inside the flat plate from the center of the heat-supplied point. Therefore, by assuming a one-dimensional model of heat conduction from the heat-supplied point, the thermal profile at the point of measurement can be qualitatively understood. Namely, a thermal profile at the point of measurement in invention 1 can be considered by assuming one-dimensional fins radially disposed about the heat-supplied point.

Assuming now that a quantity Q of heat is being supplied to a point x0 (x=0), the temperature at point x0 is Ts, and the temperature at infinity $x_\infty$ is $T_\infty$, the temperature T at point x is expressed by the following equation 1 according to the one-dimensional finned thermal conduction model:

$$T-T_\infty=(Ts-T_\infty)\exp(-SQRT(hp/kA)x) \quad \text{(Equation 1)}$$

where exp is natural logarithm, SQRT is square root, h is heat transfer coefficient, p is the boundary length of the fin, k is the thermal conductivity of a metal, and A is the cross-sectional area of the fin.

When it is assumed that the liquid is in contact with one side of the one-dimensional fin and that the other side thereof is thermally insulated, the boundary length p is roughly expressed by the sum of the width 1 of the fin and the thickness t thereof. Since 1 is a sufficiently small value relative to t, equation 1 can be expressed by equation 2:

$$T-T_\infty=(Ts-T_\infty)\exp(-SQRT(h/kt)x) \quad \text{(Equation 2)}$$

Since heat transfer coefficient h is not a physical property value, it is expressed by a function of an approximate physical value. As the average heat transfer coefficient (Nusselt number) N when a horizontal column is surrounded by a liquid is expressed by equation 3, heat transfer coefficient h can be expressed by equation 4:

$$(hl/\lambda)=N=0.1(l^3gv^{-2}Cp\mu\lambda^{-1})^{1/3} \quad \text{(Equation 3)}$$

$$h=0.1(\lambda^2 g Cp\rho^2\mu^{-1})^{1/3} \quad \text{(Equation 4)}$$

where g is gravitational acceleration, v is the kinematic viscosity (=$\mu/\rho$: $\rho$ is the density of liquid) of the liquid, Cp is the specific heat at constant temperature of the liquid, $\mu$ is the viscosity of the liquid, and $\lambda$ is the thermal conductivity of the liquid.

When equation 2 is written as $T-T_\infty=(Ts-T_\infty)\exp(-x/\tau)$, attenuation of temperature with respect to the distance x of the one-dimensional fin is characterized by an attenuation coefficient $\tau$ and, when equation 4 is applied, $\tau$ is expressed by equation 5:

$$\tau=(kt\mu^{1/3}\lambda^{-2/3}g^{-1/3}Cp^{-1/3}\rho^{-2/3})^{1/2} \quad \text{(Equation 5)}$$

Namely, it can be seen that as the heat conduction coefficient k of the fin material (container) or the fin thickness (container thickness) t increases, $\tau$ increases such that the temperature increase can be observed even at positions relatively far from the heat-supplied point. This shows that the temperature at a location distanced from the heat-supplied point may be observed with good results if the material of the container to which invention 1 is applied is selected such that the heat conduction coefficient k of the material is sufficiently larger than the heat conduction coefficient λ of the liquid (which is assumed to be water or a combustible liquid such as alcohol or gasoline), or if the thickness t of the container is sufficiently large. Examples of the material of the container suitable for invention 1 include metals such as aluminum and iron. These metals have sufficiently greater heat conduction coefficients than that of the liquid in the container. In invention 1, the distance between the heat-supplied point and the point of observation by the temperature sensor is assumed to be in the range of several millimeters to several centimeters.

From equation 5, it can be seen that the greater the heat conduction coefficient λ and density ρ of the liquid, the larger the influence on τ will be. Namely, as the heat conduction coefficient λ and density ρ of the liquid increase, τ decreases, such that the rate of cooling at the observation point increases when the quantity of heat supplied (Q) is constant. This indicates that, when there are various types of liquid with which the container may be filled, and when their thermal characteristics are different (particularly heat conduction coefficient λ and density ρ), the differences of the liquids can be detected based on their thermal characteristics.

As discussed above, it is possible to observe temperature changes reflecting the thermal characteristics (particularly, heat conduction coefficient λ and density ρ) of the liquid in a container even at an observation point that is relatively far from the heat-supplied point on the outer wall of the container where heat is supplied locally. In invention 1, the type of the liquid in the container is determined by comparing the temperature prior to heat supply and the temperature after a certain time following heat supply. The heat conduction coefficient of water is 0.63(W/mk) while those of ethanol and petroleum are 0.18(W/mk) and 0.15(W/mk), respectively, indicating that the heat conduction coefficient of water is more than 3.5 times as large as that of ethanol or petroleum. Thus, when there is water in the container, the observation point is readily cooled, while when there is a dangerous liquid, such as ethanol or petroleum, in the container, the observation point is not readily cooled. Therefore, by setting a threshold value in advance regarding the temperature difference before and after heat supply, it can be determined that the liquid in the container is safe if the threshold is exceeded and is dangerous if the threshold is not exceeded, with an alert being issued in the latter case.

In invention 1, heat is supplied externally, and the type of liquid in the container can be determined based on the measurement of the temperature of the container outer wall. Therefore, there is no need to open the container and the determination procedure is simplified, making it very suitable for baggage inspections prior to boarding an airplane and the like. Furthermore, because the temperature measurement of the outer wall of the container can be completed by making two measurements, the type of liquid in the container can be determined very simply and quickly.

For the determination of the type of liquid based on the result of temperature measurement, the measurement result (output of the temperature sensor) can be handled as digital data and processed in software terms, using an information processing device, such as a CPU. In this case, the control determination circuit may have the following configuration. Namely, the constant current circuit may include a timer, a power supply circuit capable of supplying power to the heat source, a notification signal generating circuit for outputting the alert signal to the notification means, an AD converter for converting the output of the temperature sensor into digital data, a data storage unit for recording a program and data, and an arithmetic processing unit for carrying out processes according to the program stored in the data storage unit. The program causes the arithmetic processing unit to carry out the following procedures: a first procedure in which, on the condition that no power is being supplied form the power supply circuit to the heat source, the current time is acquired from the timer and designated as t1, while data is acquired from the AD converter, designated as a value SO1, and recorded in the data storage unit; a second procedure in which the control signal to the power supply circuit is switched to an ON signal for supplying power to the heat source and, after a predetermined period of time has elapsed, the control signal to the power supply circuit is switched to an OFF signal M for not supplying power to the heat source; a third procedure in which the current time is acquired from the timer and it is determined if the acquired current time exceeds the sum of time t1 and the elapsed time t2, namely, t1+t2; a fourth procedure in which, if it is determined that the current time has exceeded time t1+t2 in the third procedure, data is acquired from the AD converter and recorded in the data storage unit as a value SO2; a fifth procedure in which a difference SO2−SO1 between value SO1 and value SO2 is calculated and compared with a predetermined threshold value, and a sixth procedure in which, depending on the result of comparison between difference SO2−SO1 and the threshold value in the fifth procedure, the alert signal is outputted from the notification signal generating circuit.

Alternatively, the output of the temperature sensor may be handled as analog data, and a determination as to whether or not the threshold value is exceeded can be made in an analog circuit. In this case, the constant current circuit includes: a lamp circuit for producing a lamp voltage upon reception of a signal indicating the start of measurement; a first latch circuit for latching the value of the temperature sensor when the absolute value of the output of the analog circuit is |V1|; a power supply circuit that starts the supply of power to the heat source when the absolute value of the output of the lamp circuit is |V2| which is greater than |V1| and that terminates the power supply when a predetermined time elapses; a second latch circuit for latching the value of the output of the temperature sensor when the voltage of the lamp circuit reaches |V3| which is larger than |V2|; a differential amplification circuit to which the outputs of the first latch circuit and the second latch circuit are inputted; and a notification signal generating circuit that compares the output of the differential amplification circuit with a predetermined threshold value and outputs the alert signal to the notification means.

The heat source and the temperature sensor may be disposed away from the wall of the container. An example of the heat source is a halogen heater, and an example of the temperature sensor is an infrared thermopile. By disposing the heat source and the temperature sensor away from the outer wall of the container, a quicker determination can be made and the problem of thermal resistance, which depends on the manner of contact in the case where contact is required, can be avoided. Namely, in the case where contact is required, thermal resistance develops or varies depending on the pressure of contact, the presence of dirt on the contact surface, and so on, making it impossible to carry out proper measurement or resulting in poor reproducibility of measurement. These possible problems can be avoided in invention 1 in which measurement can be made contactlessly.

A light-absorbing heat shield member may be disposed between the heat source and the temperature sensor. Such heat shield member enhances measurement sensitivity. When the heat source is a halogen heater and the temperature sensor is an infrared thermopile, such heat shield member may also be expected to provide the effect of shielding infrared ray.

Furthermore, a container sensor for detecting the placement of the container may be provided, and a signal from the container sensor may be used as a trigger for starting the determination process. In this way, operations can be simplified.

Invention 1 directed to the apparatus for determining the type of liquid in a container can also be grasped as invention 2 directed to a method for controlling such apparatus. Specifically, invention 2 is directed to a method for controlling an apparatus for determining the type of liquid in a container including: a heat source disposed outside a container; a temperature sensor disposed near the heat source for converting the temperature of the outer wall of the container into a voltage or current; a notification means capable of issuing an alert indicating that the content of the container is dangerous; and a constant current circuit. The method includes the steps of: storing or holding the value of an output of the temperature sensor at time t1; starting the supply of power to the heat source at time t3 which is later than time t1; terminating the power supply to the heat source at time t4 which is later than t3; storing or holding the value of an output of the temperature sensor at time t5 which is later than t3; calculating a difference between the value of the output of the temperature sensor at time t1 and the value of the output of the temperature sensor at time t5; comparing the difference with a predetermined threshold value; and issuing an alert to the notification means depending on the result of comparison between the difference and the threshold value.

In invention 2 of the control method, time t5 may be later than time t4. Namely, after a first temperature measurement is made, heat supply is started and then terminated, followed by a second temperature measurement. When the heat source is comprised of a halogen heater and the temperature sensor of an infrared thermopile, the influence of infrared scattered light associated with heat supply can be eliminated.

Other inventions are disclosed in the present specification. Invention 3 is directed to an apparatus for determining the type of liquid in a container that includes: one or a plurality of flexible films that is in contact with a container; a temperature sensor provided to the single film or one of the plurality of films; a heat source provided to the same film as or a different film from the single film or one of the plurality of films to which the temperature sensor is provided; a notification means capable of issuing an alert indicating that the content of the container is dangerous; a power supply means for supply power to the heat source; an arithmetic comparison means that acquires the output of the temperature sensor, calculates a comparison value, and compares the comparison value with a predetermined threshold value; and an alert signal output means that outputs an alert signal to the notification means depending on the result of comparison made by the arithmetic comparison means; and a control means for controlling the power supply means, the arithmetic comparison means, and the alert signal output means.

In such invention 3 of the apparatus for determining the type of liquid in a container, the heat source is provided to the flexible film which comes into contact with the container outer wall. Thus, the conduction of heat from the heat source to the container outer wall is realized via intra-solid conduction using contact, so that the container outer wall can be stably heated. Furthermore, because the temperature sensor is provided to the flexible film which is in contact with the container outer wall, the heat from the container outer wall can be conducted to the temperature sensor via intra-solid conduction using contact, so that stable temperature measurement can be achieved. The heat source does not need to be a halogen lamp and instead may be comprised of an electric resistor element, which is longer-life, whereby the life of the apparatus can be extended. Furthermore, the heat source and the temperature sensor that are provided to the flexible film can be selected from a wide variety, and they can be easily reduced in size and better adapted for mass production.

Examples of the heat source provided to the flexible film include semiconductor elements such as an electric resistor element and a Peltier element, and optical elements such as an induction heating element and a semiconductor infrared laser. The heat source, however, is not particularly limited as long as it is an element that can be mounted on the flexible film. Pattering an electric resistor element on a flexible film is advantageous from the viewpoint of mass producibility, operating life, size, stability, and so on.

Examples of the temperature sensor that can be provided to the flexible film include an electric resistor element, a thermocouple, a semiconductor element having a PN junction (bipolar semiconductor element), and other temperature-sensitive elements. However, the temperature sensor is not particularly limited as long as it is an element that can be mounted on the flexible film. Pattering an electric resistor element on the flexible film is advantageous from the viewpoint of mass producibility, operating life, size, stability, and so on.

An example of the flexible film is a polyimide film. The polyimide film is thermally and chemically stable and can be advantageously used for hermetically sealing the heat source and the temperature sensor when these are formed by patterning on the film, whereby improved oxidation resistance can be obtained. The material of the flexible film, however, is not limited to polyimide and other examples include polyamide, polyethylene terephthalate (PET), polyethylene, acrylic resin, polytetrafluoroethylene, and other organic resins.

In invention 3 of the apparatus for determining the type of liquid in a container, the film is curved when it is disposed such that the peak of the curvature is facing toward a plane on which the container is placed. Thus, when the container is placed, the heat source and the temperature sensor can be pressed against the outer wall of the container due to the flexibility of the film. As a result, a sufficient contract area can be ensured when the heat source and the temperature sensor are pressed against the outer wall of the container and thermal resistance can be reduced.

The apparatus may have either a first configuration in which the curved surface of the film is in contact with the container along a line extending in the height direction of the container, or a second configuration in which it is in contact along a line extending in the circumferential direction of the container. In the first configuration, the heat source and the temperature sensor can be disposed with a greater degree of freedom so that they can be disposed on separate films. When the heat source and the temperature sensor are disposed on separate films, thermal conduction from the heat source to the temperature sensor that is not via the container can be reduced and measurement accuracy can be improved. In the second configuration, the chances of the film being damaged when the container is placed can be reduced. Namely, when a container (such as a beverage aluminum bottle or a PET bottle) is mounted on the apparatus, the container would normally be lowered from where it is held. If the U-shaped cross-sectional plane of the curved surface is disposed opposite the bottom surface of the container (the first configuration), the bottom of the container might be caught by the U-shaped cross-sectional plane of the film and thereby damage it. However, in the case of the second configuration, it is the curved plane that the bottom surface of the container faces, so that the possible dragging of the film by the bottom of the container when the container is lowered would be absorbed by the flexibility of the film, and no damage of the film would result.

Alternatively, the film may be disposed along the outer wall of the container. Namely, although the film is disposed in the U-shape as in the previous example, the container does not come into contact with the protruding portion of the curved film but is rather held snugly in the concave portion of the U-shape. In this case, too, the heat source and the temperature sensor provided to the film can become closely attached to the outer wall of the container, and it is even possible to further press the film by using the weight of the container. Because the film is flexible, it can deform in conformity with the outer wall of the container such that the heat source and the temperature sensor can be accurately and closely attached to the outer wall of the container.

The temperature sensor may be smaller in size than the heat source. By reducing the size of the temperature sensor, the thermal capacity of the temperature sensor can be reduced, measurement time can be reduced, and accuracy of measurement can be improved.

A plurality of the heat sources may be provided, and the temperature sensor may be disposed between the multiple heat sources. By providing a plurality of heat sources around the temperature sensor, sufficient amounts of heat can be delivered to the outer wall of the container, whereby measurement time can be reduced.

Preferably, the heat source and the temperature sensor are comprised of electric resistor elements formed by patterning on the film, as mentioned above. Examples of the material of the elements include copper foil film, tungsten thin film, doped silicon, and other semiconductor materials. The resistance value of the elements may be appropriately determined as a design variation by selecting the material and hence the specific resistivity of the material, the film thickness, and sizes such as that of the line width of the pattern, for example.

In invention 3 of the apparatus for determining the type of liquid in a container, the control means controls the power supply means such that it supplies power to the heat source at time $t1$ and terminates the power supply at time $t2$ which is later than $t1$. The control means measures an output value $O1$ of the temperature sensor at time $t3$ and an output value $O2$ of the temperature sensor at time $t4$ which is later than $t3$ and $t1$, and calculates the comparison value from the output values $O2$ and $O1$. Namely, the type of liquid in the container is determined based on the temperature change in the container outer wall before and after the application of heat from the heat source.

In the case of invention 3, too, the thermal profile can be interpreted by applying the result of analysis of the thermal profile discussed in invention 1. Namely, in a one-dimensional finned thermal conduction model, when the temperature T at point x is expressed by equations 1 and 2, the average heat conduction coefficient (Nusselt number) N when a horizontal cylinder is surrounded by a liquid is expressed by equation 3, and when the heat conduction coefficient h is expressed by equation 4, attenuation constant $\tau$ that characterizes the attenuation of temperature with respect to the distance x of the one-dimensional fin (thermal profile) can be expressed by equation 5.

Namely, as the heat conduction coefficient k of the fin material (container), or the fin thickness (container thickness) t increases, $\tau$ increases, indicating that the rise in temperature can be observed at a position relatively far from the heat-supplied point. This shows that the temperature at a location distanced from the heat-supplied point can be observed with good results by selecting the material of the container to which invention 3 is applied such that the heat conduction coefficient k of the material is sufficiently greater than the heat conduction coefficient $\lambda$ of the liquid in the container (which is assumed to be water or a combustible liquid such as alcohol or gasoline), or by adopting a container having sufficient thickness t. Examples of the container material suitable for invention 3 include metals such as aluminum and iron. The heat conduction coefficient of such metals is sufficiently larger than that of the liquid in the container. In invention 3, the distance between the heat-supplied point and the temperature sensor is assumed to be in the range of several millimeters to several centimeters.

It can also be seen from equation 5 that the larger the heat conduction coefficient $\lambda$ and the density $\rho$ of the liquid, the greater the influence they have on $\rho$. Namely, as the heat conduction coefficient $\lambda$ and density $\rho$ of the liquid increase, $\tau$ becomes smaller, indicating that the rate of cooling at the observation point becomes greater if the quantity of heat supplied (Q) is constant. Thus, differences among liquids can be detected if the type of the liquid with which the container is filled varies and hence its thermal characteristics (particularly heat conduction coefficient $\lambda$ and density $\rho$) vary.

As discussed above, the temperature change that reflects the thermal characteristics of the liquid in the container (particularly heat conduction coefficient $\lambda$ and density $\rho$) can be observed at an observation point that is relatively far from the heat-supplied point where heat is locally applied to the container. In invention 3, by comparing the temperature before heat supply with the temperature a certain time after heat supply, the type of the liquid in the container is determined. The heat conduction coefficient of water is 0.63(W/mk) while those of ethanol and petroleum are 0.18(W/mk) and 0.15(W/mk), respectively, indicating that the heat conduction coefficient of water is more than 3.5 times greater. Thus, when there is water in the container, the observation point is readily cooled, while when there is ethanol, petroleum, or other dangerous liquid in the container, the observation point is not readily cooled. Therefore, by setting a threshold value regarding the temperature difference before and after heat supply, the liquid in the container can be determined to be safe if the threshold value is exceeded and to be dangerous if the threshold value is not exceeded, with an alert being issued in the latter case.

Furthermore, in invention 3, because heat is supplied externally and the type of liquid in the container can be determined based on the temperature measurement of the outer wall of the container, there is no need to open the container and determination can be made simply, making the apparatus very suitable for baggage inspections prior to boarding an airplane and the like. Furthermore, because the temperature measurement of the outer wall of the container can be completed by making two measurements, the type of liquid in the container can be determined very simply and quickly.

The control means in invention 3 may control the power supply means such that it supplies power to the heat source at time $t1$ and terminates the power supply at time $t2$ which is later than $t1$, measure an output value $O3$ of the temperature sensor at time $t6$ which is earlier than time $t5$ when the container is placed, an output value $O4$ of the temperature sensor at time $t7$ which is later than time $t5$ and earlier than time $t1$, an output value $O1$ of the temperature sensor at time $t3$, and an output value $O2$ of the temperature sensor at time $t4$ which is later than time t3 and t1, determine a correction value from the output values O4 and O3, and calculate the comparison value from the output values O2 and O1 and the correction value. In reality, the temperature of the container or the liquid therein is often very different from the measurement ambient temperature (i.e., the temperature of the temperature sensor prior to the placement of the container). For example, when the beverage is tea or coffee, the beverage is often sold or carried as heated. In such cases, the temperature reading of the temperature sensor may drift due to the influence of the temperature of the liquid in the container (temperature of the outer wall of the container). Such drift values can be predicted and corrected by measuring the sensor output values O3 and O4 before making a measurement. Namely, in accordance with the above-described invention, drifts in container temperature from the ambient temperature can be corrected and an accurate determination of the type of the liquid in the container can be made.

The prediction of drift in the sensor output due to the difference between the container temperature and the ambient temperature can be made as follows as well. Namely, the control means controls the power supply means such that it supplies power to the heat source at time t1 and terminates the power supply at time t2 which is later than t1. The control means also measures an output value O3 of the temperature sensor at time t6 which is earlier than t5 when the container is placed, an output value O1 of the temperature sensor at time t3, and an output value O2 of the temperature sensor at time t4 which is later than time t3 and t1, and then calculates the comparison value based on the output values O2, O1, and O3. Namely, the correction value is determined from the output value O3 and the output value O1 or O2, and the comparison value is calculated from the output values O1 and O2 and the correction value. This means that the measurement of the sensor output value O4 can be replaced by the measurement of O1 or O2 when determining the correction value.

Alternatively, in invention 3, a second temperature sensor is further provided that is in contact with the container away from the heat source by a distance greater than the distance between the heat source and the temperature sensor. The control means controls the power supply means such that it supplies power to the heat source at time t1 and terminates the power supply at time t2 which is later than time t1. The control means also measures an output value O1 of the temperature sensor at time t3, an output value O2 of the temperature sensor at time t4 which is later than time t3 and t1, and an output value O5 of the second temperature sensor at time t8 which is earlier than time t4, and then calculates the comparison value from the output values O2, O1, and O5. Namely, the correction value is determined from the output value O5 and the output value O1 or O2, and the comparison value is calculated from the output values O1 and O2 and the correction value. Thus, the temperature of the container itself is measured by the second temperature sensor, and corrections are made using the thus measured temperature value. The second temperature sensor may be comprised of an electric resistor element patterned on the film, as in the case of the temperature sensor. The second temperature sensor may be disposed at a position displaced from where the temperature sensor and the heat source are disposed in the circumference direction of the container.

In invention 3, a container sensor for detecting the placement of the container may be provided, whereby determination can be started by using a signal from the container sensor as a trigger. In this way, operations can be simplified.

Invention 3 of the apparatus for determining the type of liquid in a container as described above can also be grasped as invention 4 of a method for controlling such apparatus. Namely, invention 4 is directed to a method for controlling an apparatus for determining the type of liquid in a container, the apparatus including: one or a plurality of flexible films in contact with a container; a temperature sensor provided to the single film or one of the plurality of films, a heat source provided to the same film as or a different film from the single film or one of the plurality of films to which the temperature sensor is provided; a notification means capable of issuing an alert indicating that the content of the container is dangerous; a power supply means for supplying power to the heat source; an arithmetic comparison means that acquires an output of the temperature sensor, calculates a comparison value, and compares the comparison value with a predetermined threshold value; an alert signal output means for outputting an alert signal to the notification means depending on the result of comparison made by the arithmetic comparison means; and a control means for controlling the power supply means, the arithmetic comparison means, and the alert signal output means. The method includes the steps of: storing or holding an output value O1 of the temperature sensor at time t3; starting the supply of power to the heat source at time t1; terminating the power supply to the heat source at time t2 which is later than time t1; storing or holding an output value O2 of the temperature sensor at time t4 which is later than time t3 and t1; determining the comparison value from the output values O1 and O2; comparing the comparison value with the threshold value; and producing the alert signal depending on the result of comparison.

Alternatively, the invention is directed to a method for controlling an apparatus having the same structure as mentioned above for determining the type of liquid in a container, the method including the steps of: storing or holding an output value O3 of the temperature sensor at time t6 which is earlier than time t5 when the container is placed; storing or holding an output value O4 of the temperature sensor at time t7 which is later than time t5; storing or holding an output value O1 of the temperature sensor at time t3 which is later than time t7; starting the supply of power to the heat source at time t1 which is later than time t7; terminating the power supply to the heat source at time t2 which is later than time t1; storing or holding an output value O2 of the temperature sensor at time t4 which is later than time t3 and t1; determining a correction value from the output values O3 and O4; determining the comparison value from the output values O1 and O2 and the correction value; comparing the comparison value with the threshold value; and producing the alert signal depending on the result of comparison.

Alternatively, the invention is directed to a method for controlling an apparatus having the same structure as mentioned above for determining the type of liquid in a container, the method including the steps of: storing or holding an output value O3 of the temperature sensor at time t6 which is earlier than time t5 when the container is placed; storing or holding an output value O1 of the temperature sensor at time t3 which is later than time t6; starting the supply of power to the heat source at time t1 which is later than time t6; terminating the power supply to the heat source at time t2 which is later than time t1; storing or holding an output value O2 of the temperature sensor at time t4 which is later than time t3 and t1; determining the comparison value from the output values O1, O2 and O3; comparing the comparison value with the threshold value; and producing the alert signal depending on the result of comparison.

Alternatively, the invention is directed to a method for determining the type of liquid in a container, the apparatus having the same structure as mentioned above and additionally including a second temperature sensor disposed such that it is in contact with the container away from the heat source by a distance greater than the distance between the heat source and the foregoing sensor, the method including the steps of: storing or holding an output value O1 of the temperature sensor at time t3; starting the supply of power to the heat source at time t1; terminating the power supply to the heat source at time t2 which is later than time t1; storing or holding an output value O2 of the temperature sensor at time t4 which is later than time t3 and t1; storing or holding an output value O5 of the second temperature sensor at time t8 which is earlier than time t4; determining the comparison value from the output values O1, O2, and O5; comparing the comparison value with the threshold value; and producing the alert signal depending on the result of comparison. These control methods according to invention 4 can be applied to the aforementioned apparatuses according to invention 3.

Effects of the Invention

Invention 1 and 2 provide techniques for quickly determining the type of liquid in a container from the outside regardless of the material of the container and preferably in a contactless manner. Inventions 3 and 4 provide methods for quickly determining the type of liquid in a container from the outside thereof regardless of the material thereof, whereby the outer wall of the can be stably heated and the temperature near the heated portion can be stably measured. The inventions also extend the life of the apparatus and achieve reductions in size of the heated portion and the temperature measured portion. The apparatuses according to the inventions are well-adapted to mass production.

BEST MODES FOR CARRYING OUT THE INVENTION

Embodiment 1

Embodiments of the invention will be hereafter described with reference to the drawings. FIG. 1 shows a block diagram of an example of the structure of an apparatus for determining the type of liquid in a container according to an embodiment of the invention. The apparatus for determining the type of liquid in a container according to the present embodiment includes a halogen heater 102, an infrared thermopile 103, a slit 104, a heat shield plate 105, a control circuit 106, LED display devices 107a, 107b, and 107c, and a container sensor 108, all of which are disposed outside the container.

The container 101 is an electrically conductive container made of aluminum, for example. The halogen heater 102 is a heat source for irradiating the surface of the container 101 with an infrared ray via the opening provided by the slit 104. Thus, the halogen heater 102 supplies heat energy to the surface of the container 101. A plurality of thermocouples are connected in series to the infrared thermopile 103 so as to form a contactless temperature sensor, with the cold junction in contact with the case and the hot junction in contact with an infrared absorbing member. The infrared thermopile 103 is disposed at a distance of approximately 2 cm from the halogen heater 102.

The slit 104 is an optical member for limiting the irradiation light from the halogen heater 102 such that a specific region on the surface of the container 101 is irradiated therewith. It may be comprised of a member having a circular or rectangular opening of several millimeters. The heat shield plate 105 blocks the transmission of heat from the halogen heater 102 to the infrared thermopile 103.

The control circuit 106 controls the supply of power to the halogen heater 102, measures the output of the infrared thermopile 103, and determines the type of liquid in a container. The control circuit 106 is also connected to the LED display devices 107a, 107b, and 107c, by which the result of determination is displayed.

The control circuit 106 includes a CPU (central processing unit) 109, a heat-source drive circuit 110, an AD converter 111, a ROM (read-only memory), a RAM (random access memory), a timer 114, a container detection circuit 115, and a display control circuit 117. The CPU 109 is comprised of a general-purpose arithmetic processing device and can execute processes in accordance with a predetermined program. The heat-source drive circuit 110, which is controlled by the CPU 109, supplies power to the halogen heater 102. The AD converter 111 converts the output of the infrared thermopile 103 into digital data, which is fed to the CPU 109. The container detection circuit 115 controls the container sensor 108 so as to detect the presence or absence of the container 101 on a container support member (not shown). The timer 114 is controlled by the CPU 109 and is used for measuring the passage of time. The RAM 113 is a temporary data storage device. It stores programs or data loaded from the ROM 112 and ensures a work area for the execution of the programs. The ROM 112 records programs or data used in the apparatus. The ROM 112 may be replaced with other forms of memory, such as a hard disc drive. The operation of a control program recorded in the ROM 112 will be described later. While the control program recorded in the ROM 112 is intangible by itself, it makes up the apparatus organically together with other hardware resources and provides the function of determining the type of liquid, as will be described later. Thus, the control program is a constituent requirement necessary for specifying the apparatus according to the invention. The display control circuit 117 controls the display on the LED display devices 107a, 107b, and 107c.

The LED display devices 107a, 107b, and 107c display the condition of the apparatus and the result of measurement of the type of liquid in the container 101 obtained by the apparatus. The LED display device 107a displays in green, the LED display device 107b displays in blue, and the LED display device 107c displays in red, for example. While the following description is directed to an example in which the condition of the apparatus and the result of measurement are indicated (displayed) by the LED display devices 107a, 107b, and 107c, other notification means may be adopted as needed. For example, messages may be displayed on an LCD, or a buzzer may be used for emitting sound upon detection of abnormality.

The container sensor 108 is a sensor for detecting the placement of the container 101 on the container support member. It may be comprised of an optical sensor having a light-emitting portion and a light-receiving portion. It may also be comprised of other forms of sensor, such as a proximity sensor.

FIG. 2 shows a chart illustrating how the temperature on the surface of the container changes in the apparatus according to the present embodiment. The horizontal axis shows the time and the vertical axis shows the sensor output. The chart shows the temperature change (changes in the sensor output) over time in a graph. At time t2, the halogen heater 102 is turned on (i.e., supply of power from the heat-source drive circuit 110 is initiated). At time t3, the halogen heater 102 is turned off (i.e., supply of power from the heat-source drive circuit 110 is stopped). As the halogen heater 102 is turned off, the temperature on the surface of the container 101 gradually decreases. A line 118 shows the thermal profile on the surface of the container 101 when the liquid therein is ethanol. As discussed above, the higher the heat conductivity of the liquid, the higher the rate of cooling on the surface of the container 101. Thus, the water, even though heat is fed thereto, is cooled swiftly such that the temperature on the surface of the container 101 does not increase much (line 119). On the other hand, ethanol has a heat conductivity smaller than that of water, so that the temperature on the surface of the container becomes somewhat higher with the same quantity of heat applied. The rate at which the liquid is cooled upon turning off the halogen heater 102 is also somewhat higher for water. As a result, a difference of $\Delta V$ is produced as the sensor output in terms of the surface temperature of the container 101 at time t4.

Thus, in the apparatus according to the present embodiment, the type of liquid in a container is determined based on the temperature change on the surface of the container 101 before and after the application of heat. The temperature on the container surface is measured at time t1 and t4, a temperature difference is calculated, and a predetermined threshold value is set. If the difference exceeds the threshold value, the liquid is determined to be not water (and rather a dangerous material such as alcohol, petroleum, or gasoline). If the difference is below the threshold value, the liquid is determined to be safe water (or beverage consisting primarily of water). The threshold value may be determined by actually measuring the value of the aforementioned difference $\Delta$ and adding $\Delta V/2$ to the expected value of difference of water. When the halogen heater 102 is actually turned on, much noise is caused in the infrared thermopile 103 due to the reflection of infrared ray from the surface of the container 101. This noise, however, is not shown in FIG. 2 for the sake of simplicity of description.

FIG. 3 shows a flowchart of an example of a method for determining the type of liquid in a container using the apparatus for determining the type of liquid in a container according to Embodiment 1. The procedure including the processes described below can be described by a computer program that is recorded in the ROM 112. In the present specification, programs are considered part of the apparatus of the invention as long as they are recorded in the ROM 112 or other storage devices. While the following description involves an example in which the following processes are executed by a computer program, it goes without saying that similar processes can be realized through other control means, such as sequence control and automatic control based on hardware.

At step 120, it is determined whether or not the container 101 is detected. If not, a green lamp is activated indicating that the apparatus is in a standby mode (step 121). The step 120 is repeated until no container is detected. When a container is detected, the routine proceeds to step 122.

At step 122, the output of the temperature sensor (infrared thermopile 103) is measured. The output value (analog value) is converted into a digital value by the AD converter 111, and the digital value is recorded in the RAM 113, for example, as a measured value A.

A standby period of 0.5 seconds, for example, is allowed to elapse (step 123), and then a control signal (ON signal) to be sent to the heat-source drive circuit 110 for turning on the halogen heater 102 is produced (step 124). Then, at step 125, it is determined whether or not two seconds, for example, has elapsed. If two seconds has elapsed, the halogen heater 102 is turned off at step 126 (i.e., an OFF signal is sent to the heat-source drive circuit as a control signal).

Thereafter, a standby period of 0.5 second is allowed to elapse (step 127), and the output of the temperature sensor (infrared thermopile 103) is measured (step 128). The output value (analog value) is converted into a digital value by the AD converter 111, and the digital value is recorded in the RAM 113, for example, as a measured value B.

The difference between the variables A and B is then calculated, and it is determined whether this value is greater than a predetermined threshold value (step 129). If B−A is determined to be smaller than the threshold value at step 129, it can be determined that the liquid in the container is a safe liquid consisting primarily of water, and therefore a blue lamp is activated (step 131). Conversely, if it is determined at step 129 that B−A is greater than the threshold value, the liquid in the container cannot be determined to be a safe liquid consisting primarily of water. Therefore, a red lamp is activated indicating the presence of abnormality (step 130). At steps 130 and 131, a standby period of approximately two seconds is provided so as to ensure the time for the operator to recognize the nature of each indication. In this way, the type of liquid in the container can be determined.

In the apparatus for determining the type of liquid in a container according to the present embodiment, the type of the liquid content can be easily determined even when the container is made of metal such as aluminum. The determination process is started upon placing the container 101 on the apparatus, and whether or not the content is a safe liquid consisting primarily of water can be easily determined in view of the blue and red lamps. Because a single measurement can be completed in several seconds, the apparatus can be advantageously utilized for inspections that must be carried out quickly, such as the baggage inspection before boarding an airplane.

The foregoing descriptions of the duration of time for halogen lamp irradiation and the standby periods are for exemplary purposes only and may be changed as needed.

While the invention has been described above with reference to Embodiment 1, obviously the invention is not limited to the foregoing embodiment and may be changed or modified within the spirit of the invention.

For example, while in the foregoing Embodiment 1 an example of control was described in which software was employed by the control circuit 106 including the CPU 109, the output of the temperature sensor (infrared thermopile 103) may be used as analog data, and a control circuit 130 may be comprised of an electronic circuit that carries out analog calculations, as shown in FIG. 4. In the control circuit 130 shown in FIG. 4, upon detecting the placement of the container 101 by the container surface 108, a lamp voltage is generated by a lamp circuit 131 and is fed to a comparator 132. The comparator 132, with reference to reference voltages V1, V2, and V3 (V1<V2<V3), turns on a latch control signal to a first latch circuit 134 when the input reaches V1. In response to the turning-on of the latch control signal, the first latch circuit 134 latches the instantaneous sensor output. The output of the first latch circuit 134 is fed to the—input of a differential amplifier 136. When the input to the comparator 132 reaches V2, the comparator 132 turns on the control signal to the heat-source drive circuit 133. In response to the turning-on of the control signal, the heat-source drive circuit 133 turns on the halogen heater 102 and then turns it off two seconds later, for example. When the input to the comparator 132 reaches V3, the comparator 132 turns on the latch control signal to a second latch circuit 135. In response to the turning-on of the latch control signal, the second latch circuit 135 latches the instantaneous sensor output. The output of the second latch circuit 135 is fed to the+input of a differential amplifier 136, which amplifies the difference in input voltages and produces an output. The input of the differential amplifier 136 is fed to a comparator 137, which, with reference to a threshold voltage Vth, turns on the red LED display device 107c if the input is greater than Vth and turns on the blue LED display device 107b if it is below Vth. The comparator 137 is adapted such that, in the absence of the control signal (latch control signal to the second latch circuit 135), which is outputted when the voltage (lamp voltage) inputted to the comparator 132 becomes V3, no display (in red or blue) is made by the LED display device 107b or 107c, and that in other cases a green display (by the LED display device 107a) is made indicating that a standby mode is present. Thus, the time when the lamp voltage reached V3 can be indicated with the red and the blue lamps.

While in the foregoing Embodiment 1 an infrared thermopile has been described as an example of the temperature sensor, this is merely for illustrative purposes only and other temperature sensors, such as a thermocouple, a temperature-sensitive resistor element, or the like, can be used as desired. The heat source is also not limited to the halogen heater but may be realized with a heat-generating resistor, a Peltier device, an infrared laser, or the like as desired.

Furthermore, in the foregoing Embodiment 1, the temperature sensor and the heat source were spaced apart from each other. However, this is merely an example and, while the temperature sensor and the heat source are preferably spaced apart from the container from the viewpoint of increased speed of determination process and determination reproducibility, as mentioned above, the present invention does not necessarily require that the temperature sensor and the heat source be disposed away from the container. Namely, the temperature sensor and/or the heat source may be in contact with the container.

While in the foregoing Embodiment 1 the container 101 was comprised of a metal container of, e.g., aluminum. The material of the container, however, is not limited to metals as long as the heat conductivity of the container is sufficiently larger than the heat conductivity of the liquid therein, or as long as the container is sufficiently thick. For example, the container may be comprised of a nonmetallic container such as a PET bottle and still the liquid determining apparatus and method of controlling the same according to the invention can be employed. The requirements regarding the heat conductivity of the container and its thickness depend on how far the temperature observation point on the container outer wall is distanced from the heated region. If the temperature observed point is sufficiently close to the heated region, the heat conductivity of the container may be on the same order as that of the liquid in the container, and also the thickness of the container may be on the order of the thickness of practical PET bottles.

Embodiment 2

In the following, a second embodiment of the invention will be described with reference to the drawings. FIG. 5 shows a block diagram of an example of the structure of an apparatus for determining the type of liquid in a container (to be hereafter referred to as a liquid determining apparatus) according to Embodiment 2. The liquid determining apparatus according to Embodiment 2 includes a flexible film 202 that is in contact with the outer wall of a container 201, a heat source 203 provided to the film 202, a temperature sensor 204 provided to the film 202, a control circuit 206, LED display devices 207a, 207b, and 207c, and a container sensor 208.

The container 201 is an electrically conductive container made of aluminum, for example. The liquid determining apparatus according to Embodiment 2 is suitable for use with conductive containers; however, the container 201 is not limited to conductive containers. For example, an insulating container such as a PET bottle may be subjected to the liquid determining apparatus of Embodiment 2. The size and shape of the container 201 are not particularly limited. As will be described later, the shape and size of the container 201 may be random as long as they are such that the heat source 203 and temperature sensor 204 provided to the film 202 will come into contact with its outer wall. It is noted, however, that the liquid needs to be in the container such that it is at least in contact with the portion thereof corresponding to where the heat source 203 and temperature sensor 204 provided to the film 202 are in contact with the outer wall of the container.

The film 202 is a flexible plastic film, for example, such as a film of polyimide. Polyimide has a proper flexibility and resilience and is thermally and chemically stable, making it suitable as the film 202 for the present invention. The material of the film 202, however, is not limited to polyimide and other plastic materials may be used, such as polyamide, polyethylene, polyethylene terephthalate, acrylic resin, polytetrafluoroethylene, and ABS resin, for example, as desired. The material of the film is not limited to plastics either, and any insulating material may be used as desired as long as it has flexibility, such as paper, thin-film glass, and so on. The film 202 is disposed in physical contact with the container 201 as will be described later.

The heat source 203 is comprised of an electric resistor patterned on the film 202, as will be described later in detail. The functional requirements of the heat source 203 include that it can be installed on the film 202 and that it can generate proper amounts of heat under proper control. Thus, any means can be selected as the heat source 203 as long as it satisfies these requirements. Examples include a Peltier device, a semiconductor laser, and an inductive heating element (consisting of a heated member and an inductive element).

The temperature sensor 204 is comprised of an electric resistor element patterned on the film 202, as will be described later. The functional requirements of the temperature sensor 204 are that it can be installed on the film 202 and that it is sensitive to temperature (i.e., it can produce sufficient output signal in response to temperature change). Thus, any means can be selected as the temperature sensor 204 for Embodiment 2 as long as it satisfies these conditions. Examples include a thermocouple and a PN junction of a semiconductor device.

The control circuit 206 controls the supply of power to the heat source 203 and measures the output of the temperature sensor 204 to determine the type of liquid in the container. The control circuit 206 is connected to the LED display devices 207a, 207b, and 207c, on which the result of determination is displayed.

The control circuit 206 includes a CPU (central processing unit) 209, a heat-source drive circuit 210, an AD converter 211, a ROM (read-only memory) 212, a RAM (random-access memory) 213, a timer 214, a container detection circuit 215, a constant current circuit 216, and a display control circuit 217. The CPU 209 is comprised of a general-purpose arithmetic processing device capable of executing processes according to a predetermined program. The heat-source drive circuit 210 is controlled by the CPU 209 and supplies power to the heat source 203. The AD converter 211 converts the output of the temperature sensor 204 into digital data, which is outputted to the CPU 209. The container detection circuit 215 controls the container sensor 208 and detects the presence or absence of the container 201 disposed on the container supporting member (not shown). The timer 214, which is controlled by the CPU 209, is used for measuring the passage of time. The RAM 213 is a temporary data storage device, where programs or data loaded form the ROM 212 are retained and where a work area for the execution of a program is ensured. The ROM 212 records programs or data used by the apparatus. The ROM 212 may be replaced with other memory devices, such as a hard disc drive. The operation of the control program recorded in the ROM 212 will be described later. While the control program recorded in the ROM 212 is intangible by itself, it is recorded in the ROM 212, constitutes an organic part of the apparatus together with its hardware resources, and plays a role in the liquid type determination function of the apparatus, as will be described later. Thus, the control program is a constituent requirement for specifying the apparatus according to the invention. The constant current circuit 216 supplies a constant current to the temperature sensor 204 of Embodiment 2. The electric resistor element illustrated as an example of the temperature sensor 204 of Embodiment 2 is a passive element and it does not output any signal by itself. Rather, a constant current is supplied to the temperature sensor 204 (electric resistor element) from the constant current circuit 216 and its resistance value is detected in the form of voltage. When the temperature sensor is comprised of an active element that produces an output voltage (signal) by itself, the constant current circuit 216 would not be necessary. The display control circuit 217 controls the display on the LED display devices 207a, 207b, and 207c.

The LED display devices 207a, 207b, and 207c display the result of determination of the type of liquid in the container 201 made by the apparatus as well as the condition thereof, as will be described later. The LED display device 207a emits green light, the LED display device 207b emits blue light, and the LED display device 207c emits red light, for example. While the following example describes the LED display devices 207a, 207b, and 207c giving notification (displaying) of the condition of the apparatus or the result of measurement, any other notifying means may be used. For example, messages may be displayed on an LCD, or a buzzer may emit sound upon detection of abnormality.

The container sensor 208 is a sensor for detecting the presence of the container 201 disposed on the container supporting member. An example is an optical sensor consisting of a light-emitting portion and a light-receiving portion. Other sensors, such as a proximity sensor, may be used.

FIG. 6 shows a schematic perspective view of an example of a container disposed portion of the liquid determining apparatus according to Embodiment 2. A container disposed portion 218 includes a stage 218a on which the container 201 is to be disposed. At the center of the stage 218a, a slit 218b is provided for the alignment of the position of the container 201. Inside the slit 218b is disposed a film 202 curved in the U-shape, with the bottom of the U facing upward.

The container 201 is disposed such that it is partly buried in the slit 218b, with the upper part of the container placed in the back. As the container 201 is aligned with respect to the slit 218b, the container 201 can be easily aligned such that its outer wall come into contact with the film 202 without fail.

Because the stage 218a is disposed at an angle, as shown, the container 201 can be stably disposed with the bottom thereof abutting against a front face plate 218c. A stopper may be provided to the front face plate 218c so that the bottom of the container 201 can be reliably abutted against the front face plate 218c. That the stage 218a is disposed at an angle means that the container 201 is also disposed at an angle, which provides the advantage that the liquid when there is only a little of it therein can be collected at the bottom of the container. In such cases, the probability of the liquid when there is only a little of it remaining at a portion of the container where the heat source 203 and temperature sensor 204 of the film 202 are in contact can be increased by disposing the film 202 at near the bottom of the container 201. Thus, the type of liquid can be reliably determined even when there is only a little of the liquid in the container 201 or when the size of the container 201 varies.

FIG. 7 shows a perspective view of the film 202 that is curved in the U-shape and disposed with the bottom of the U facing upward. At the convex portion of the curvature (where the container 201 is in contact) are disposed the heat source 203 and the temperature sensor 204.

FIG. 8 shows a cross section of the film 202 when the container 201 is disposed at the container disposed portion 218 shown in FIG. 6. The state of the film 202 prior to the placement of the container 201 is indicated by the broken line. As shown, because the film 202 is flexible, the convex portion of the film 202 is pushed down when the container 201 is disposed, such that the convex portion becomes deformed in conformity of the profile of the outer wall of the container 201. As a result, the heat source 203 and the temperature sensor 204 come into contact with the outer wall of the container 202 without fail, thus ensuring contact between them. Furthermore, because the film 202 is flexible, the heat source 203 and the temperature sensor 204 are pressed against the container 201, so that the heat resistance at the contact portion can be reduced and a stable supply of heat and temperature measurement can be ensured.

FIG. 9(a) shows a plan view of an example of the heat source 203 and the temperature sensor 204 provided to the film 202. The heat source 203 and the temperature sensor 204 are comprised of electric resistor elements patterned on the film 202. The heat source 203 and the temperature sensor 204 are connected to individual terminals 203a and 204a via wiring lines 203b and 204b, respectively. It goes without saying that the terminals and wiring lines are all patterned as well. It is also obvious that after the heat source 203 and the temperature sensor 204, the individual terminals 203a and 204a, and the wiring lines 203b and 204b have been patterned, they are shielded with the same or a different material from the film 202. Pattern production methods are well-known and their detailed description is omitted herein. Examples of the material of the heat source 203, temperature sensor 204, terminals 203a and 204a, and wiring lines 203b and 204b include metals such as copper and tungsten, and semiconductors such as doped silicon.

FIG. 9(b) shows a partly enlarged plan view of a portion B of FIG. 9(a). The heat source 203 can be produced by forming a fine zigzag pattern, as shown. The line width of such pattern is a matter of design variation and may be determined as appropriate depending on the quantity of heat required and the specific resistivity of the material. The same goes for the temperature sensor 204.

In the example shown in FIG. 9, there is one each of the heat source 203 and the temperature sensor 204, both having substantially the same size. However, other suitable variations are possible. FIGS. 10 to 12 show plan views of variations of the heat source 203 and the temperature sensor 204 provided to the film 202. In the variation shown in FIG. 10, the temperature sensor 204 is patterned to be larger than the heat source 203, whereby the heat capacity of the temperature sensor can be reduced and the rate of response during temperature measurement can be improved. In the variation shown in FIG. 11, a plurality of heat sources 203 are provided where they are disposed such that the temperature sensor 204 is sandwiched thereby. In this case, sufficient heat amounts can be supplied, so that determination can be made at high speed and with accuracy. In the variation shown in FIG. 12, the film 202 for the heat source 203 and that for the temperature sensor 204 are separately provided. In this case, the path of heat that is not via the container 201, i.e., the path of thermal flow through the film 202, can be blocked, whereby the accuracy of reliability of measurement can be improved.

While in the foregoing examples the film 202 is curved in the U-shape with the bottom of the U facing upward, the film 202 may be disposed in other manners. For example, the film 202 may be curved in the U-shape and the bottom of the U may be facing downward, namely, the convex portion facing upward. In this case, the film can be deformed in conformity to the profile of the outer wall of the container using the weight of the container 201 itself.

Alternatively, the film 202 may be disposed as shown in FIG. 13 where it is rotated by 90° with respect to the example of FIG. 6, such that the film 202 is in contact with the container 201 along the circumference thereof. In this case, the chances of the film 202 being damaged upon placement can be reduced. Namely, if the container 201 is disposed as shown, the bottom of the container 201 could hit the film 202. If that happens in the example of FIG. 6, the bottom of the container 201 could drag on the curved film cross-sectionally, which would damage the film 202. However, when the film 202 is disposed as shown in FIG. 13, even if the bottom of the container 201 hits the film 202, the contact would be on the curved surface of the film 202, so that the curved surface would merely deform and not be damaged. An example of the patterning of the heat source 203 and the temperature sensor 204 for the case of FIG. 13 is shown in FIG. 14.

FIG. 15 is a graph showing how the temperature on the surface of the container changes in the liquid determining apparatus according to Embodiment 2. The graph shows the change in temperature (namely, change in sensor output) over time in which time is shown on the horizontal axis and sensor output on the vertical axis. At time t1, the heat source 203 is turned on (by starting the supply of power from the heat-source drive circuit 210). At time t2, the heat source 203 is turned off (by terminating the supply of power from the heat-source drive circuit 210). When the heat source 203 is turned on, the surface temperature of the container 201 increases (i.e., the sensor output increases); when the heat source 203 is turned off, the surface temperature of the container 201 gradually drops. A line 219a shows the thermal profile on the surface of the container 201 when the liquid in the container 201 is ethanol. A line 219b shows the thermal profile on the surface of the container 201 when the liquid is water. As discussed earlier, the higher the heat conduction coefficient of the liquid, the higher the rate of cooling on the surface of the container 201. Thus, the water is rapidly cooled even though it is fed with heat, such that the surface temperature of the container 201 does not rise much (line 219b). On the other hand, in the case of ethanol, because ethanol's heat conduction coefficient is smaller than that of water, the surface temperature of the container becomes higher with the same quantity of heat applied. The cooling rate upon turning off the heat source 203 is also slightly higher for water. As a result, the difference $\Delta V$ is caused in the sensor output indicating the surface temperature of the container 201 at time t4.

Thus, in accordance with the liquid determining apparatus of Embodiment 2, the type of liquid in the container is determined based on the temperature change on the surface of the container 201 before and after the application of heat. The container surface temperatures are measured at time t3 and time t4, the difference between them is calculated as a comparison value, and a predetermined threshold value is set. If the comparison value is greater than the threshold value, the liquid is determined to be not water (i.e., alcohol, petroleum, gasoline, or other dangerous substance). If the comparison value is smaller than the threshold value, the liquid is determined to be safe water (or a beverage consisting primarily of water). The threshold value may be determined by actually measuring the value of the aforementioned difference $\Delta V$ and adding $\Delta V/2$ to the expected value of the difference for water. Noise could be produced upon actually turning on the heat source 203; in FIG. 15, however, such noise is not shown for the sake of simplicity of explanation.

In the example shown in FIG. 15, the initial measurement time for obtaining the comparison value is earlier than time t1 (namely, t3), and the second measurement time is later than time t2 (namely, t4). These are merely examples and the times of measurement are not limited to t3 or t4 as long as the times are such that the comparison value obtained reflects the thermal characteristics of the liquid in the container. For example, the initial measurement time may be at the same time as, or later than, t1. And the second measurement time may be at any time later than the first measurement time (it is noted, however, that the second measurement time must be later than time t1 if the first measurement time is earlier than time t1). Thus, any time in the period stretching over t1 or between t1 and t2 when the container surface temperature is rising, the period stretching over t2 when the container surface temperature is changing, or the period after t2 when the container surface temperature is dropping (i.e., period between the first measurement and the second measurement) may be selected.

FIG. 16 shows a flowchart of an example of the method for determining a liquid in a container using the liquid determining apparatus according to Embodiment 2. A procedure involving the processes described below can be implemented as a computer program that is recorded in the aforementioned ROM 212. In the present specification, such program, as long as it is recorded in the ROM 212 or other storage device, constitutes a part of the apparatus of the invention. While an example will be described below in which the processes are executed using a computer program, it goes without saying that the same processes can be realized using other control means, such as sequence control, and hardware-based automatic control, for example.

At step 220, it is determined whether or not the container 201 is detected. If no container is detected, the green lamp is turned on, indicating that the apparatus is in a standby state (step 221), and step 220 is repeated until no container is detected. If a container is detected, the routine proceeds to step 222.

At step 222, the output of the temperature sensor 204 is measured. The output value (O1) from the temperature sensor 204, which is an analog value, is converted into a digital value by the AD converter 211, and a resultant value A is recorded in the RAM 213, for example.

Then, a standby period of 0.5 second, for example, is allowed to elapse (step 223), followed by the production of a control signal (ON signal) to the heat-source drive circuit 210 for turning on the heat source 203 (step 224). Then, it is determined at step 225 whether or not two seconds, for example, has elapsed, and if the time has elapsed, the heat source 203 is turned off at step 226 (i.e., the control signal to the heat-source drive circuit is rendered into an OFF signal).

After the apparatus stands by for 0.5 second (step 227), the output of the temperature sensor 204 is measured (step 228). The output value (O2) of the temperature sensor 204 is an analog value, which is converted into a digital value by the AD converter 211 and a resultant value B is recorded in the RAM 213, for example.

Then, the difference between the values A and B is calculated, and it is determined whether the difference value (comparison value) is greater or smaller than a predetermined threshold value (step 229). If B−A is smaller than the threshold value at step 229, the liquid in the container can be considered to be a safe liquid consisting primarily of water, and the blue lamp is turned on (step 231). Conversely, if B−A is determined to be greater than the threshold value at step 229, the liquid in the container cannot be considered to be a safe liquid consisting primarily of water, and therefore the red lamp is turned on (step 230), indicating abnormality. At steps 230 and 231, a standby period of 2 seconds, for example, is allocated for the operator to recognize the nature of notification. Thereafter, the routine returns to step 220 and the above-described routine is repeated. In this way, the type of liquid in the container can be determined.

As mentioned earlier, the first sensor output measurement (of value A) and the second sensor output measurement (of value B) may be carried out at any time as long as the comparison value obtained reflects the thermal characteristics of the liquid in the container. Namely, the measurement of value A at step 222 may be performed after power is turned on at step 224. The measurement of value B at step 228 may be performed before power is turned off at step 226. The measurement of values A and B at step 222 and step 228, respectively, may be performed after power is turned off at step 226. However, a proper time must be provided between the measurement of value A and the measurement of value B. When a measurement is performed in the period in which the container surface temperature is decreasing, the comparison value B−A becomes a negative number. In this case, therefore, the absolute value of B−A must be used for the determination at step 229.

In accordance with the apparatus for determining the type of liquid in a container according to Embodiment 2, the type of liquid can be easily determined even if the liquid is in a metal container, such as that of aluminum. The determination procedure begins upon placing of the container 201 on the apparatus. Whether or not the liquid in the container consists primarily of water and is safe can be easily determined based on the illumination of the blue or red lamp. A single measurement can be completed within several seconds, making the apparatus suitable for applications where expeditious processing is required, such as during baggage inspection prior to boarding an airplane.

In accordance with the liquid-type determination apparatus according to Embodiment 2, the heat source 203 and the temperature sensor 204 are patterned on the film 202, which is bent in the U-shape and disposed such that the heat source 203 and the temperature sensor 204 can be in contact with the container 201. Thus, direct contact between the container 201 and the heat source or temperature sensor is ensured, whereby stable supply of heat and temperature measurement can be realized. Because the heat source and the temperature sensor are formed on the film by patterning, the apparatus can be reduced in size and mass-produced easily. Furthermore, stable elements can be employed for the heat source and the temperature sensor, so that the life of the apparatus can be extended.

The on/off times and the standby time of the heat source described above are merely examples and may be changed as needed.

While the invention has been described above with reference to Embodiment 2, obviously the invention is not limited to the foregoing embodiment, and various changes or modifications may be made within the spirit of the invention.

For example, Embodiment 2 was described with reference to a control method in the case where the container temperature is substantially equal to the ambient temperature. The container temperature, however, is in practice often different from the ambient temperature. In such cases, the following improvements may be added.

With reference to FIG. 17, the sensor output when the container temperature is different from the ambient temperature is described. When the time at which the container 201 is placed is t5, the sensor output prior to t5 corresponds to the ambient temperature. As the container 201 is placed at t5, the sensor output increases as shown by the broken line. A broken line 240a corresponds to a case where the container temperature is e.g. 50° C. A broken line 240b corresponds to a case where the container temperature is e.g. 40° C. And a broken line 240c corresponds to a case where the container temperature is e.g. 30° C. The higher the container temperature, the higher the asymptotic value toward which the sensor output increases. If there are such fluctuations in sensor output, an accurate determination based on measurement through the above-described control may be hindered. Thus, the determination control is preferably carried out after the sensor output fluctuations due to the container temperature are eliminated. However, the determination must be made quickly and as soon as the container 201 is placed.

In the following, thermal profiles upon heating of the container surface when there are sensor output fluctuations due to the container temperature are considered. The solid line shown in the graph of FIG. 18 plots the sensor output upon heating of the container surface for a certain period of time when there is a sensor output fluctuation. The broken line shows the sensor output fluctuations due to the container temperature. The heat source 203 is turned on at time t1 and turned off at time t2. The sensor output is measured at time t3 (sensor output O1 in Embodiment 2 (measured value A)) and at time t4 (sensor output O2 in Embodiment 2 (measured value B)). The measurement times t3 and t4 may be changed, as mentioned above. In this case, the sensor output fluctuation (baseline fluctuation) ΔVb due to the container temperature is included in the difference ΔV in measurement values between times t4 and t3. If ΔVb cannot be ignored with respect to the margin from the threshold value, the validity of determination is called into question. Thus, ΔVb needs to be corrected before determination by measuring or predicting ΔVb in one way or another.

FIG. 19 shows a flowchart of an example of determination control when there is baseline fluctuation. At the beginning of the program, the value T0 is initialized to zero (step 250), and then the output of the temperature sensor is measured before detecting a container (step 251). A measurement value (O3) of the sensor output is recorded in the RAM 213, for example, as a value T1, as at step 222 of FIG. 16. It is then determined whether or not the difference between a previously measured value and the value T0 is below a predetermined value so as to make sure the sensor output is stable (steps 252 and 253). Once the sensor output is stable, the presence or absence of a container is detected, and, if no container is detected, the green lamp is turned on indicating that measurement can be made (steps 254 to 256). When the sensor output is measured for the stability confirmation purpose, the value T1 is recorded in a buffer and the like as a previous value T0 for the subsequent measurement (steps 253 and 255). If a container is detected, the sensor output is measured (step 258) after a standby period of 0.5 second, for example (step 257). A resultant measurement value (O4) of the sensor output is recorded in the RAM 213 as a value T2 as previously. A correction value C corresponding to the baseline fluctuation ΔVb is determined from the difference between the values T2 and T1 (step 259). During the determination of the correction value C, a pre-recorded correction table 260 can be referred to. The correction method, however, is not limited to the one involving the correction table 260 and the correction value may be determined by calculations using an appropriate model function based on the values T1 and T2. After the correction value C is determined, the value A (sensor output value O1) and the value B (sensor output value O2) are measured as in the case of FIG. 16 (steps 261 to 266). However, in this case, since a proper time has elapsed since the container was placed, the standby period in step 223 in FIG. 16 is not needed. After the values A and B are measured, the correction value C is added and the resultant value is compared with the threshold value (step 267). Steps 268 and 269 are similar to steps 230 and 231 of FIG. 16. These controls allow an accurate determination to be made even if there was a baseline fluctuation. The times at which the values A and B are measured are not particularly limited as long as a comparison value that reflects the thermal characteristics of the liquid in the container can be obtained, as in the previous embodiment.

During the controls shown in FIG. 19, the measurement of the value T2 (sensor output value O4) is not necessarily required. Namely, the correction value C may be determined using value A or B instead of value T2. More specifically, the correction value C can be determined based on value T1 and value A, or value T1 and value B, and then the comparison value can be determined based on the correction value C and values A and B. During the determination of the correction value C, a correction table may be employed, or the correction value may be determined by calculations using an appropriate model function, as in the previous case.

Alternatively, a second temperature sensor 270 can be disposed at a sufficient distance from the heat source 203 as shown in FIG. 20, separately from the temperature sensor in Embodiment 2. For the measurement of the output of the temperature sensor 270, an AD converter 271 and a constant current circuit 272 are provided. In this case, the container temperature is measured by the second temperature sensor at the same times of measurement for the values A and B so as to measure the baseline fluctuation. The measurement timing for the second temperature sensor 270, however, is not limited to the above example and may be determined as desired. In this case, a correction table or corrective calculations for the correction value C in accordance with the measurement timing must be provided.

In the previous example, a software-based control by the control circuit 206 including the CPU 209 was described. It is possible, however, to handle the output of the temperature sensor as analog data and to construct the control circuit 280 with an electronic circuit performing analog calculations, as shown in FIG. 21. In a control circuit 280 shown in FIG. 21, as the placement of the container 201 is detected by the container sensor 208, a lamp voltage is generated by the lamp circuit 281 and fed to a comparator 282. The comparator 282, with reference to reference voltages V1, V2, and V3 (V1<V2<V3), turns on a latch control signal to a first latch circuit 284 if the input reaches V1. The first latch circuit 284, in response to the turning-on of the latch control signal, latches the instantaneous sensor output. The output of the first latch circuit 284 is inputted to the—input of a differential amplifier 286. If the input to the comparator 282 reaches V2, the comparator 282 turns on a control signal to a heat-source drive circuit 283. In response to the turning-on of the control signal, the heat-source drive circuit 283 turns on the heat source 203, and then turns it off two seconds later, for example. If the input to the comparator 282 reaches V3, the comparator 282 turns on a latch control signal to a second latch circuit 285. In response to the turning-on of the latch control signal, the second latch circuit 285 latches the instantaneous sensor output. The output of the second latch circuit 285 is fed to the +input to a differential amplifier 286, which amplifies the difference in input voltages. The input to the differential amplifier 286 is inputted to a comparator 287. The comparator 287, with reference to the threshold voltage Vth, turns on the red LED display device 207c if the input is greater than Vth and turns on the blue LED display device 207b if the input is not greater than Vth. The comparator 287 is adapted such that, in the absence of the control signal (latch control signal to the second latch circuit 285) that is outputted upon the voltage (lamp voltage) inputted to the comparator 282 reaching V3, neither the LED display devices 207b nor 207c (red or blue) are turned on and instead the green display (LED display device 207a) is turned on, indicating a standby. Thus, the determination upon the lamp voltage reaching V3 can be indicated by the illumination of the red or blue lamp. There is also provided a constant current circuit 288 for producing a sensor output.

INDUSTRIAL APPLICABILITY

The invention relates to an apparatus and method for determining the safety of the content of a beverage container brought aboard transportation means such as aircraft simply and reliably without opening the container. The invention can be applied in industries relating to inspection equipment for inspecting the content of containers. The apparatus for determining the type of liquid in a container according to the invention can also be used by transportation facilities in airline industries, for example.

EXPLANATION OF THE NUMERALS

Figure 1:
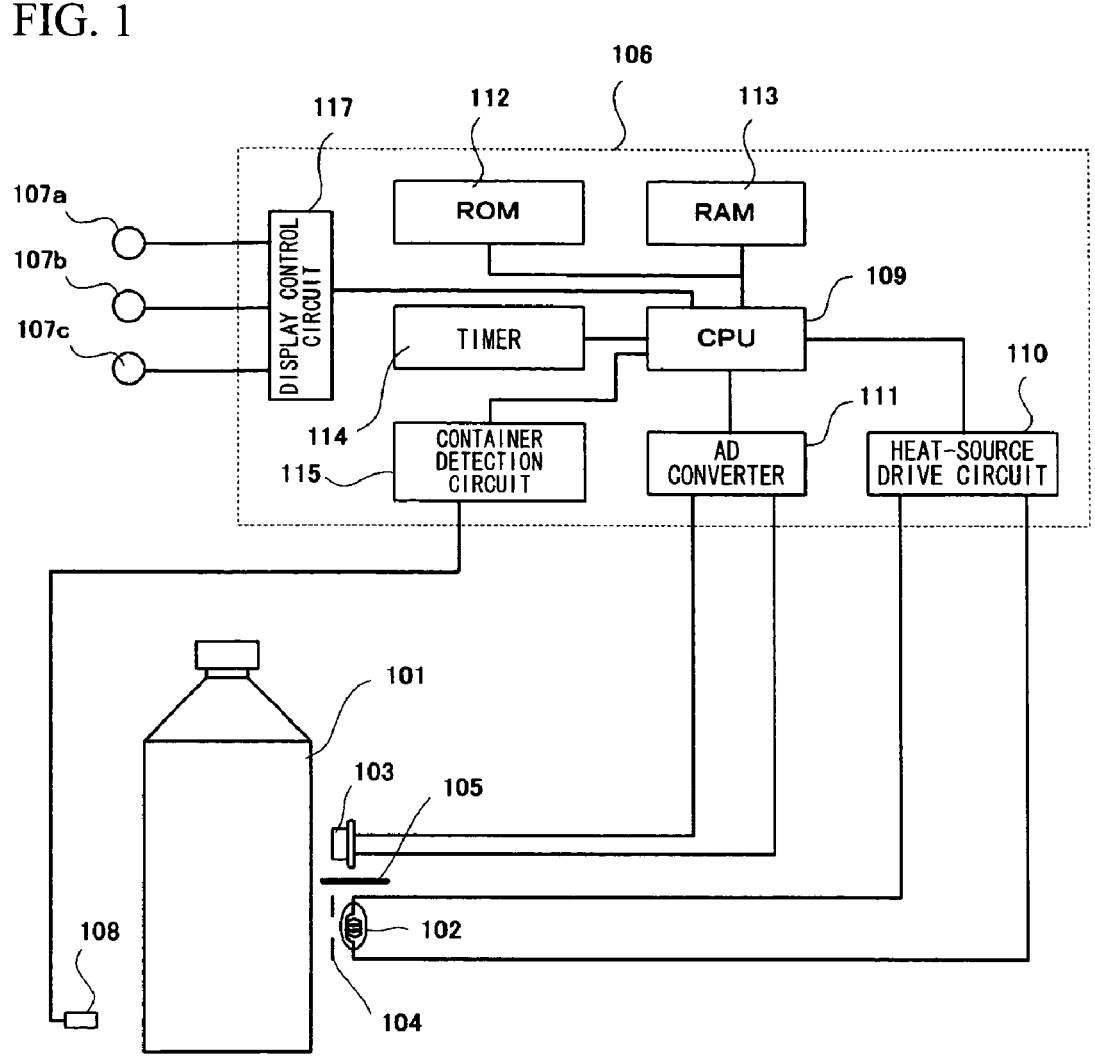
FIG. 1 shows a block diagram of an example of the structure of an apparatus for determining the type of liquid in a container according to Embodiment 1 of the invention.
Figure 2:
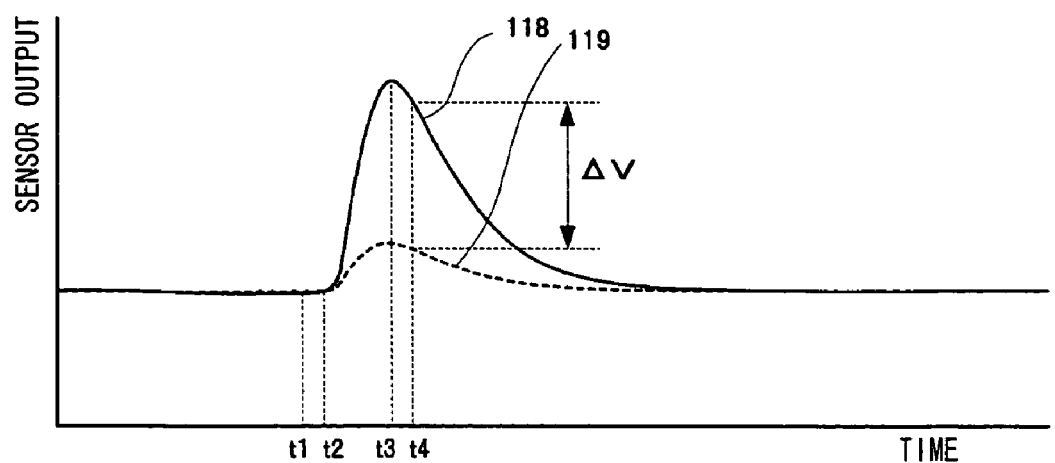
FIG. 2 shows a chart illustrating how the surface temperature of a container changes in the apparatus according to Embodiment 1.
Figure 3:
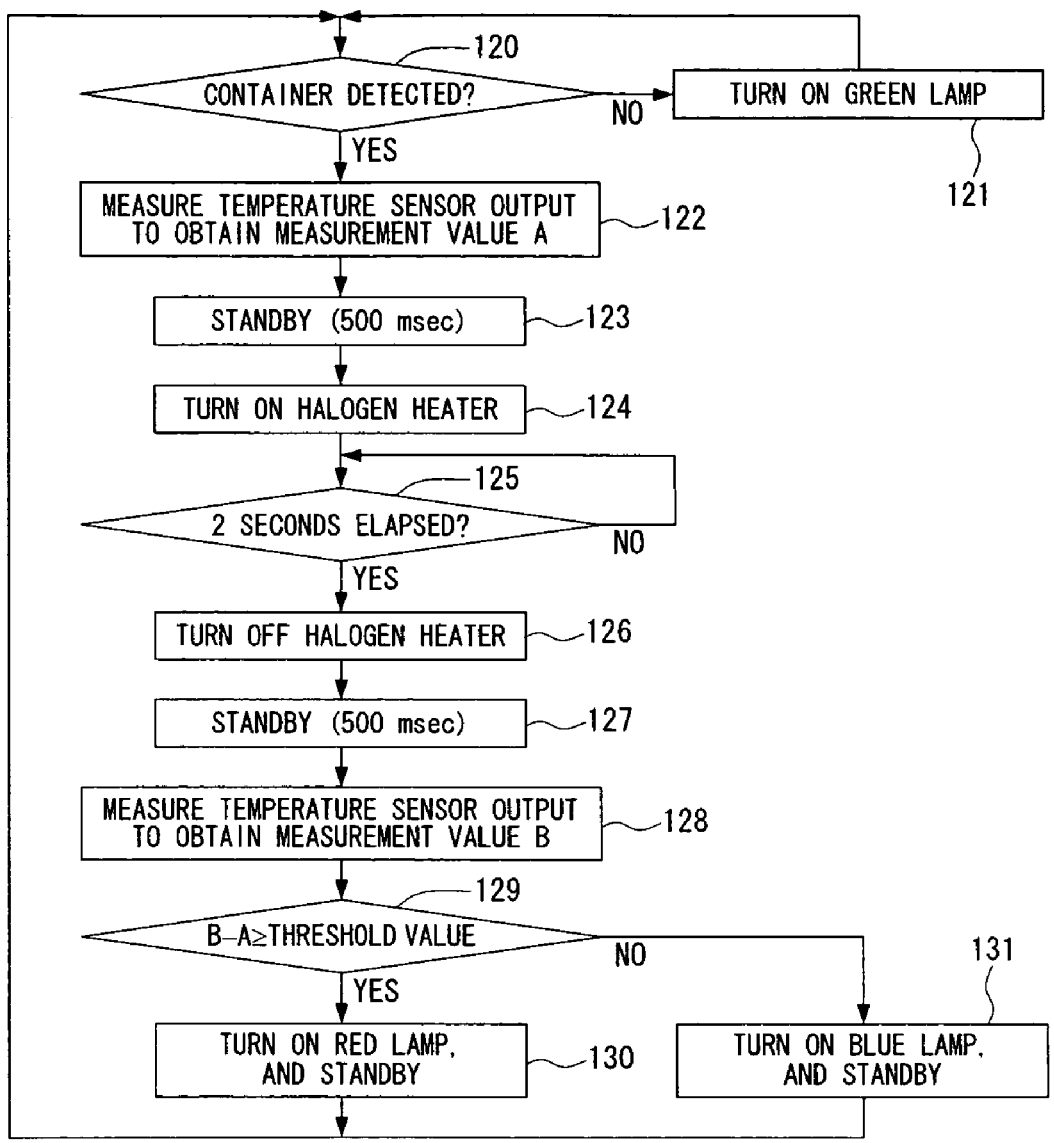
FIG. 3 shows a flowchart of an example of a method for determining the type of liquid in a container in the liquid-type determination apparatus according to Embodiment 1.
Figure 4:
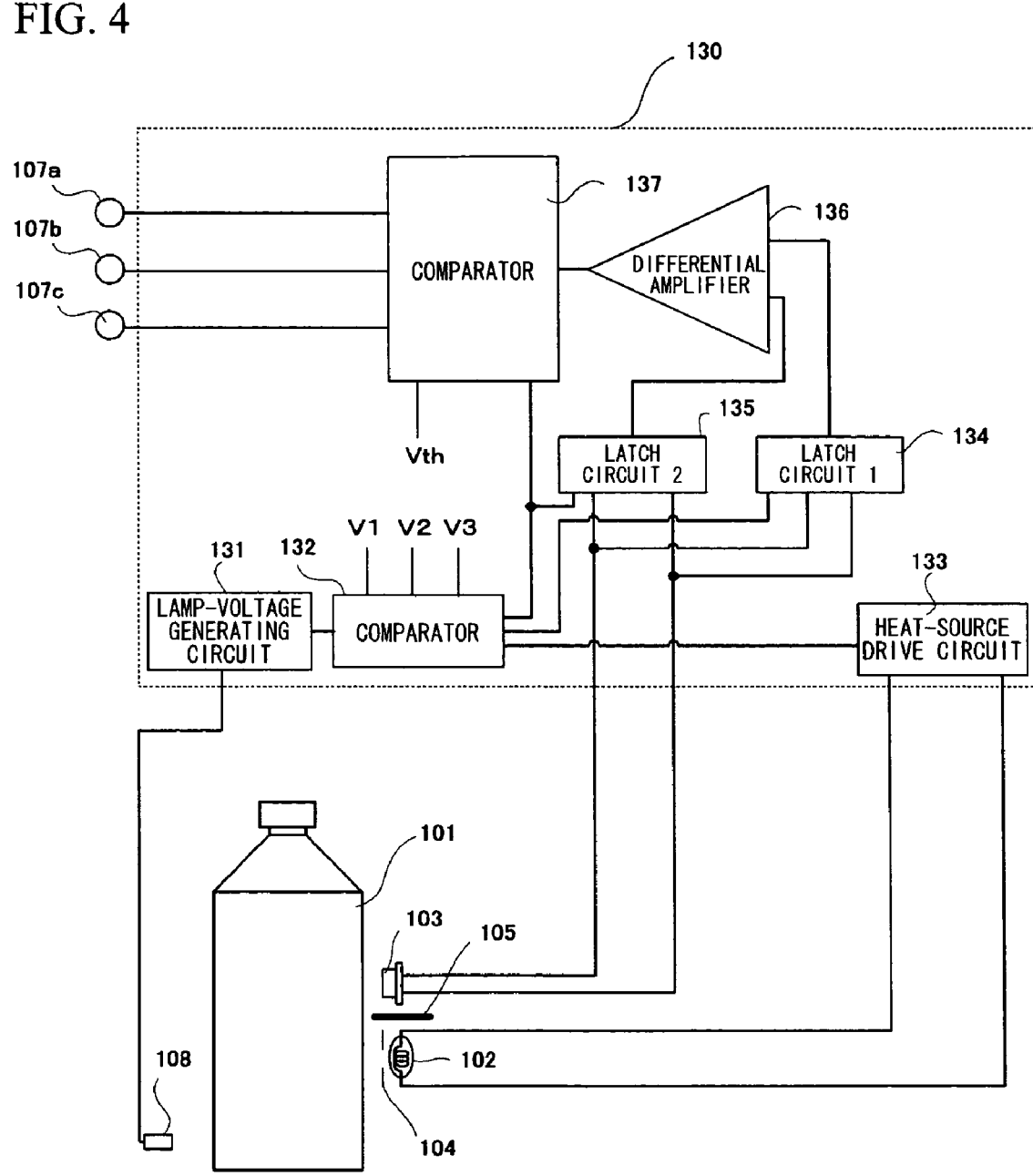
FIG. 4 shows a block diagram of another example of the structure of an apparatus for determining the type of liquid in a container according to the invention.
Figure 5:
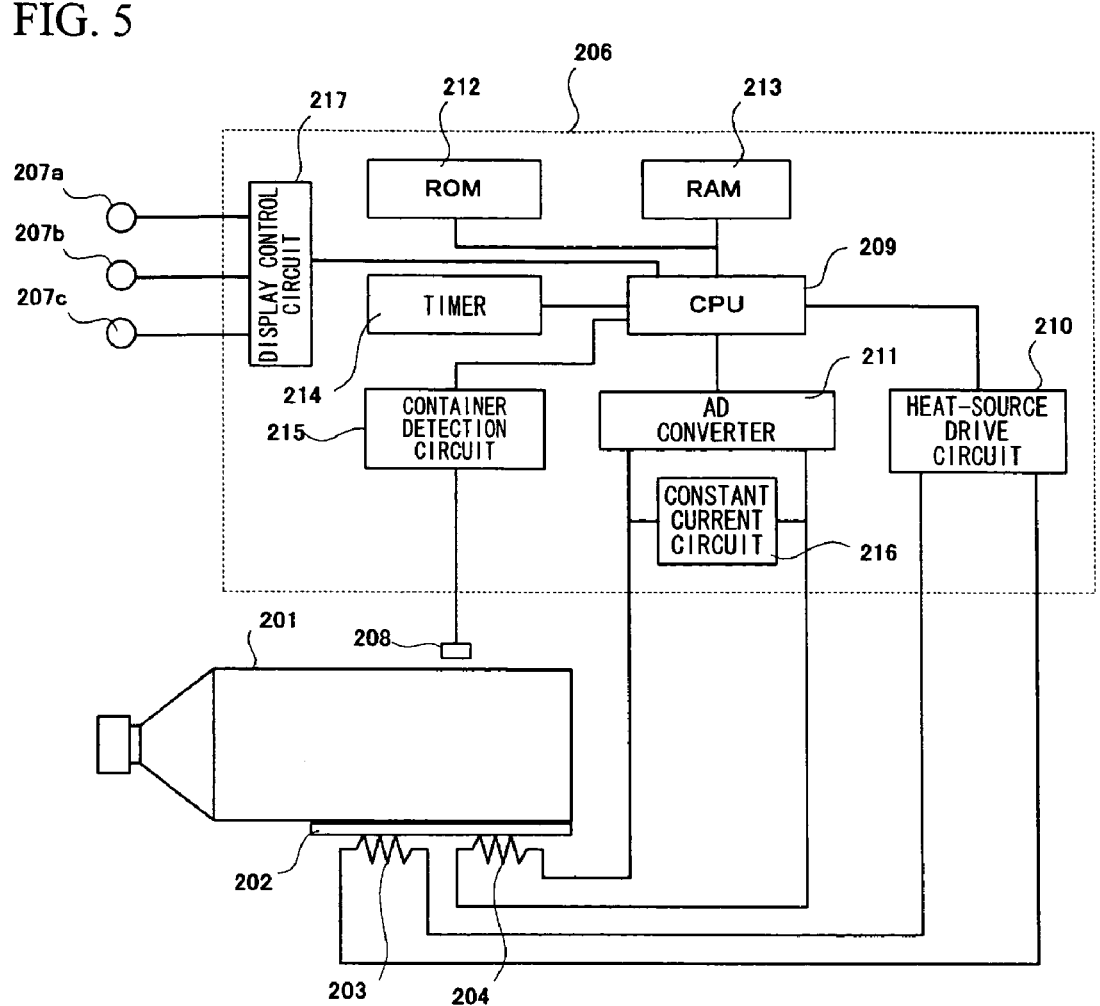
FIG. 5 shows a block diagram of an example of the structure of an apparatus for determining the type of liquid in a container according to Embodiment 2.
Figure 6:
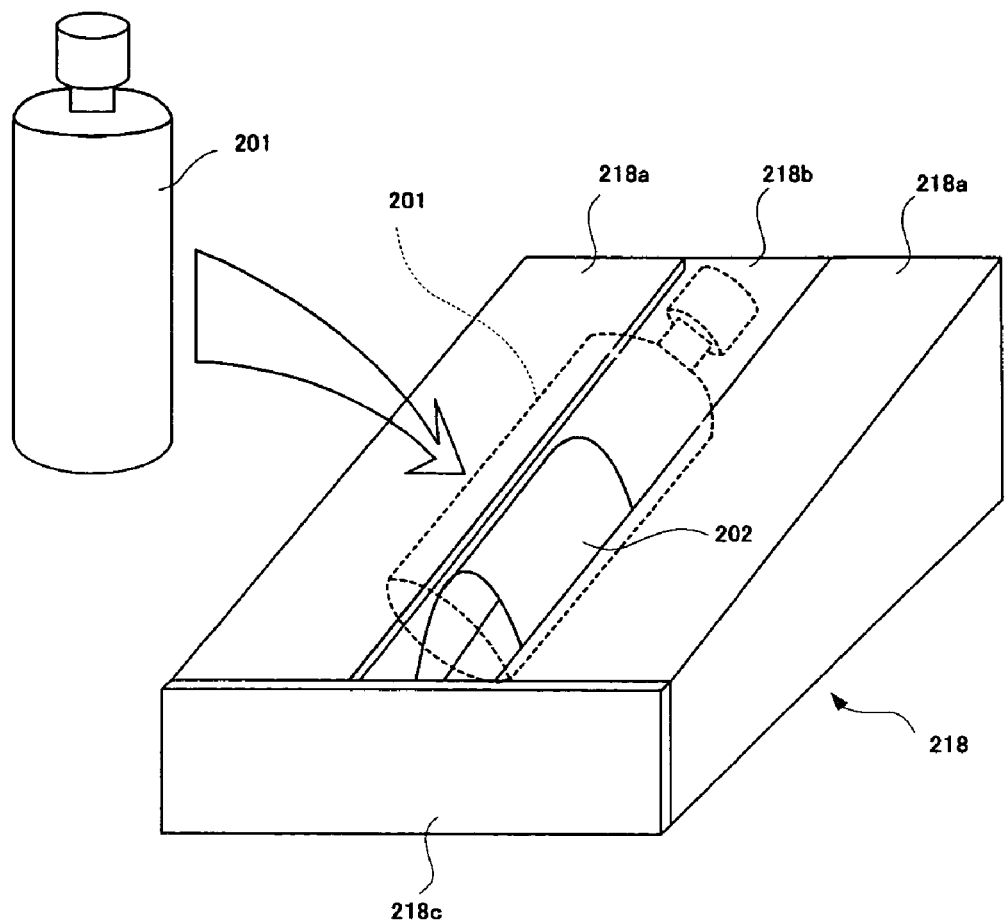
FIG. 6 shows a schematic perspective view of an example of a container disposed portion of the liquid determining apparatus according to Embodiment 2.
Figure 7:
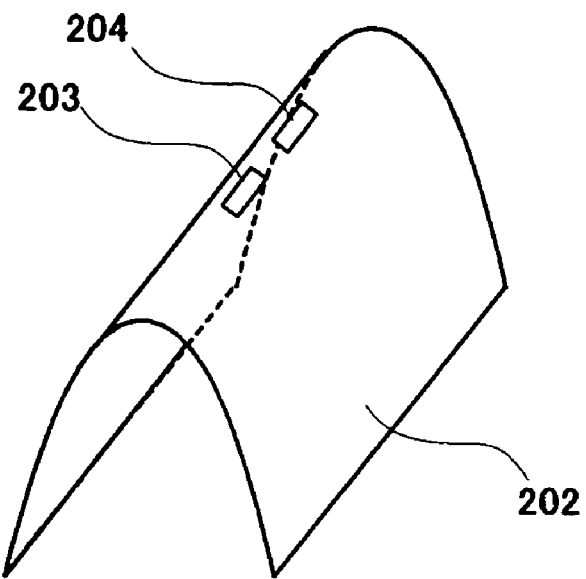
FIG. 7 shows a perspective view of a film 202 curved in the U-shape and disposed with the convex portion thereof facing upward.
Figure 8:
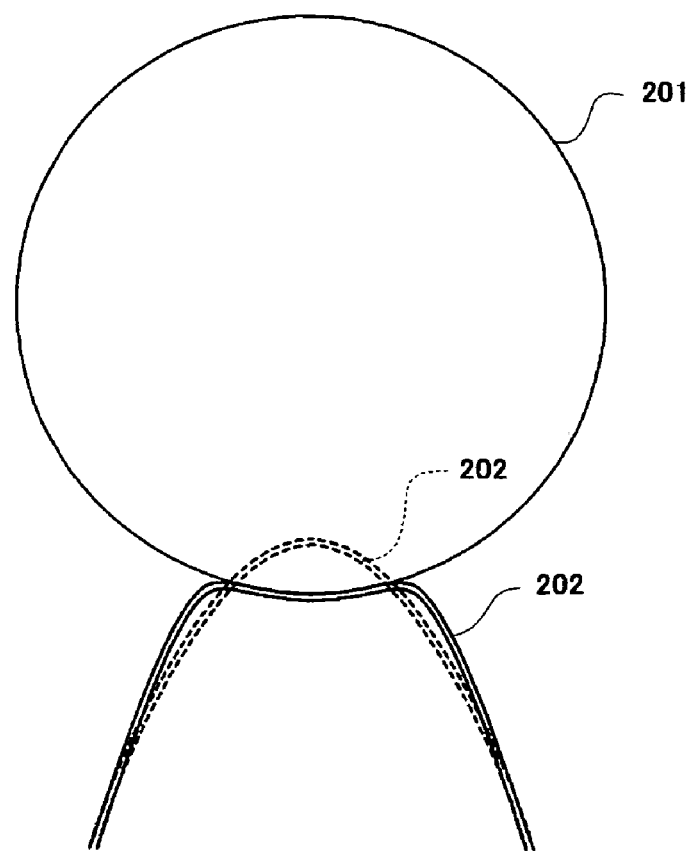
FIG. 8 shows a cross-sectional view of the film 202 when a container 201 is placed on the container disposed portion 218.
Figure 9:
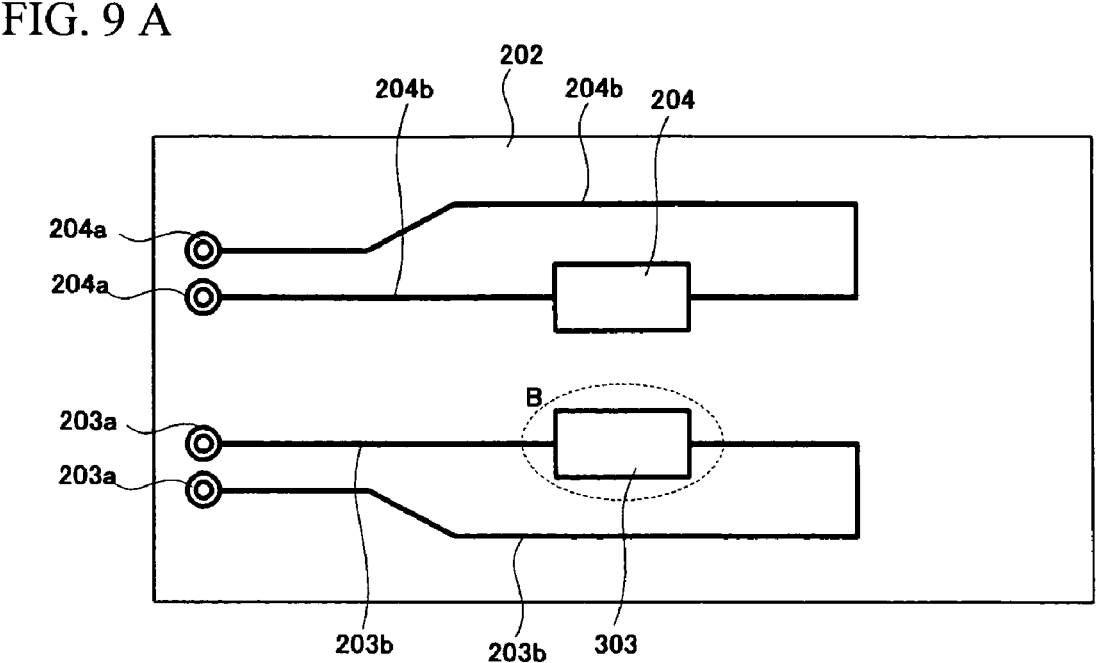
FIG. 9(a) shows a plan view of an example of a heat source 203 and a temperature sensor 204 provided to the film 202.
FIG. 9(b) shows a partly enlarged plan view of a portion B of FIG. 9(a).
Figure 9:
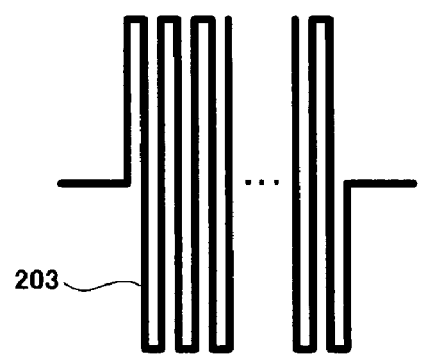
Figure 10:
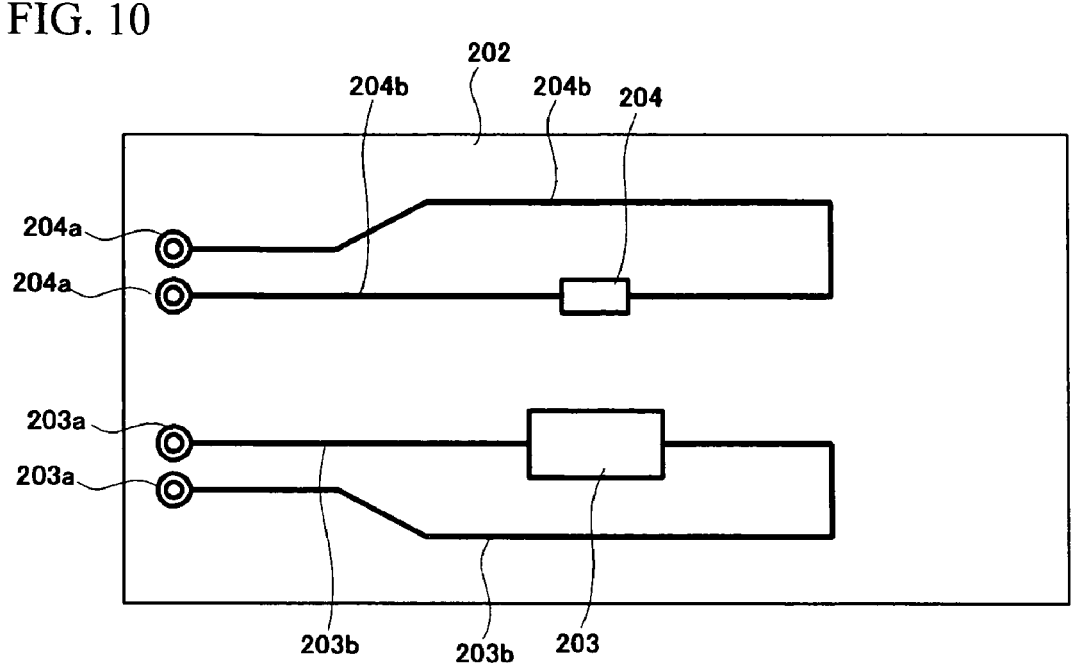
FIG. 10 shows a plan view of a variation of the heat source 203 and temperature sensor 204 provided to the film 202.
Figure 11:
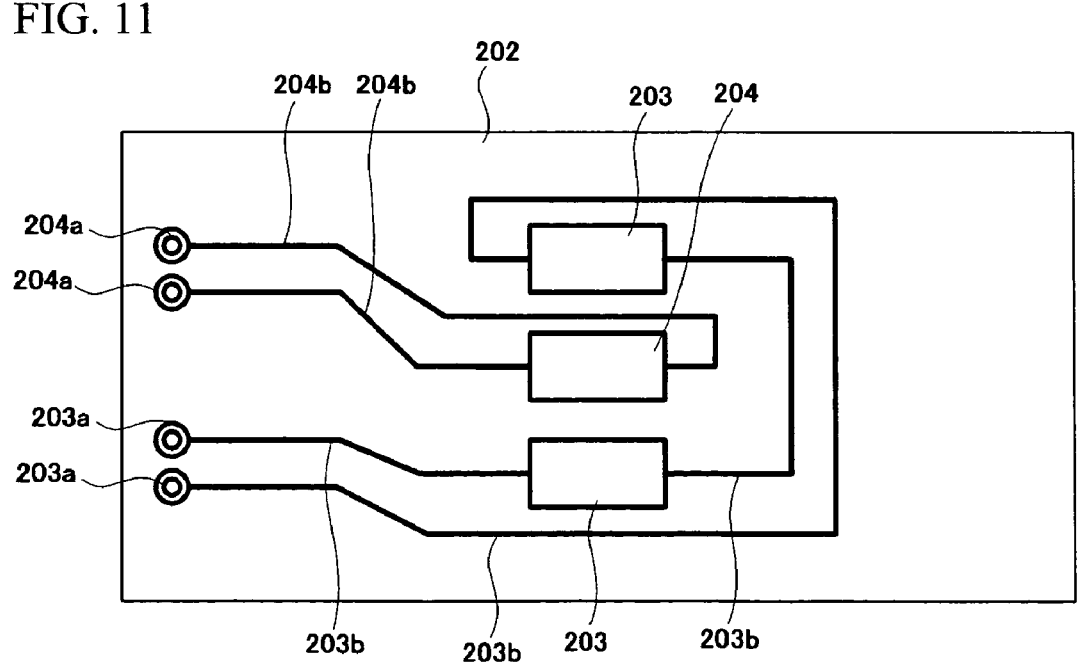
FIG. 11 shows a plan view of a variation of the heat source 203 and temperature sensor 204 provided to the film 202.
Figure 12:
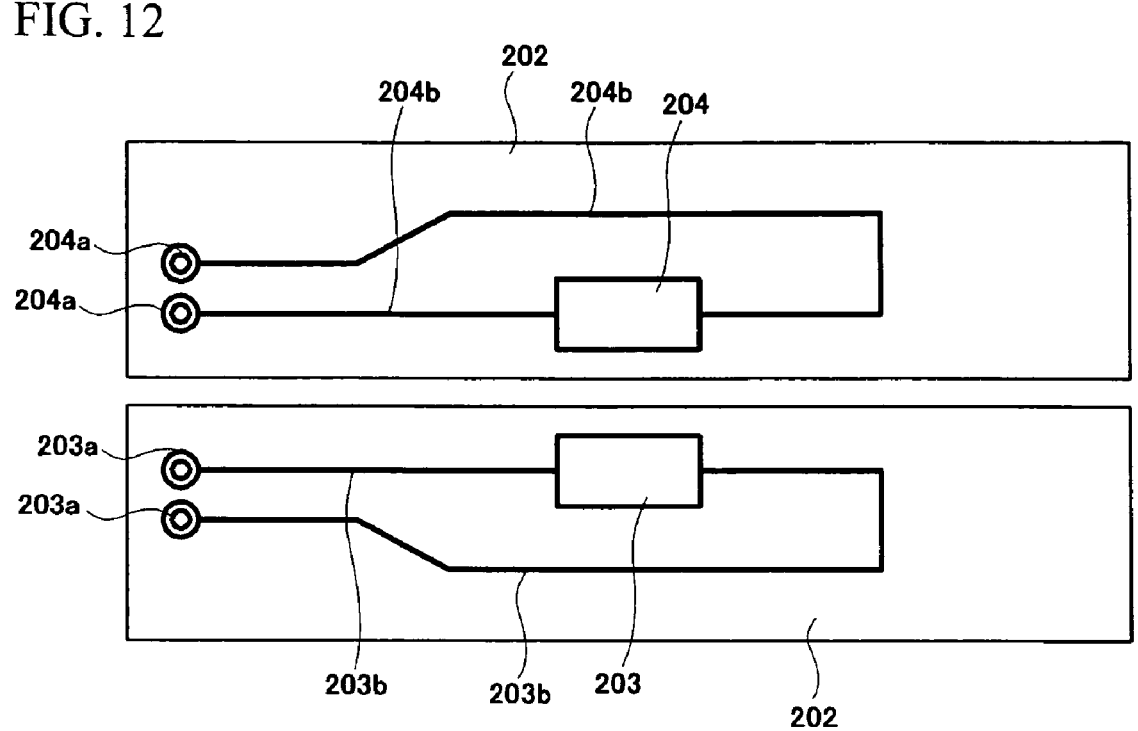
FIG. 12 show a plan view of a variation of the heat source 203 and temperature sensor 204 provided to the film 202.
Figure 13:
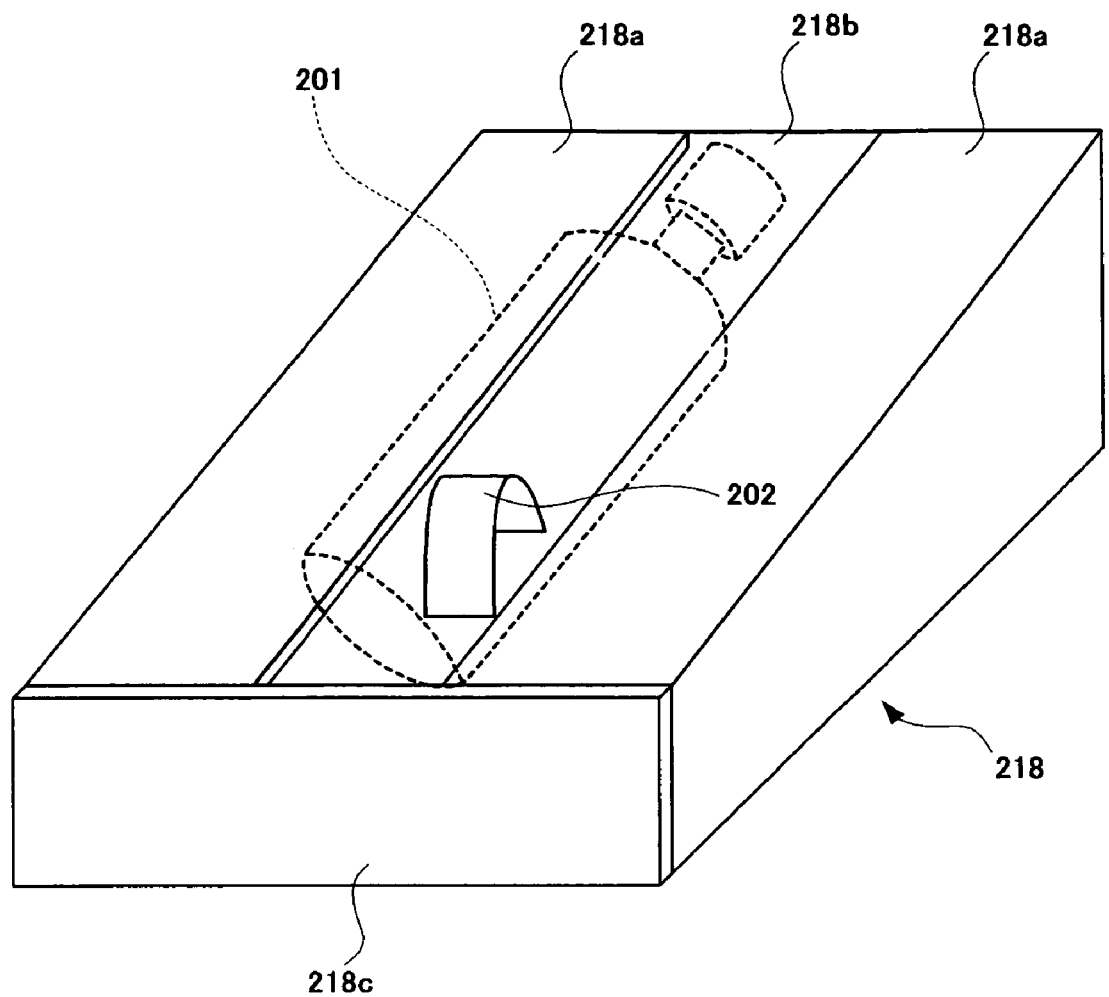
FIG. 13 shows a schematic perspective view of another example of the container disposed portion of the liquid determining apparatus according to Embodiment 2 of the invention.
Figure 14:
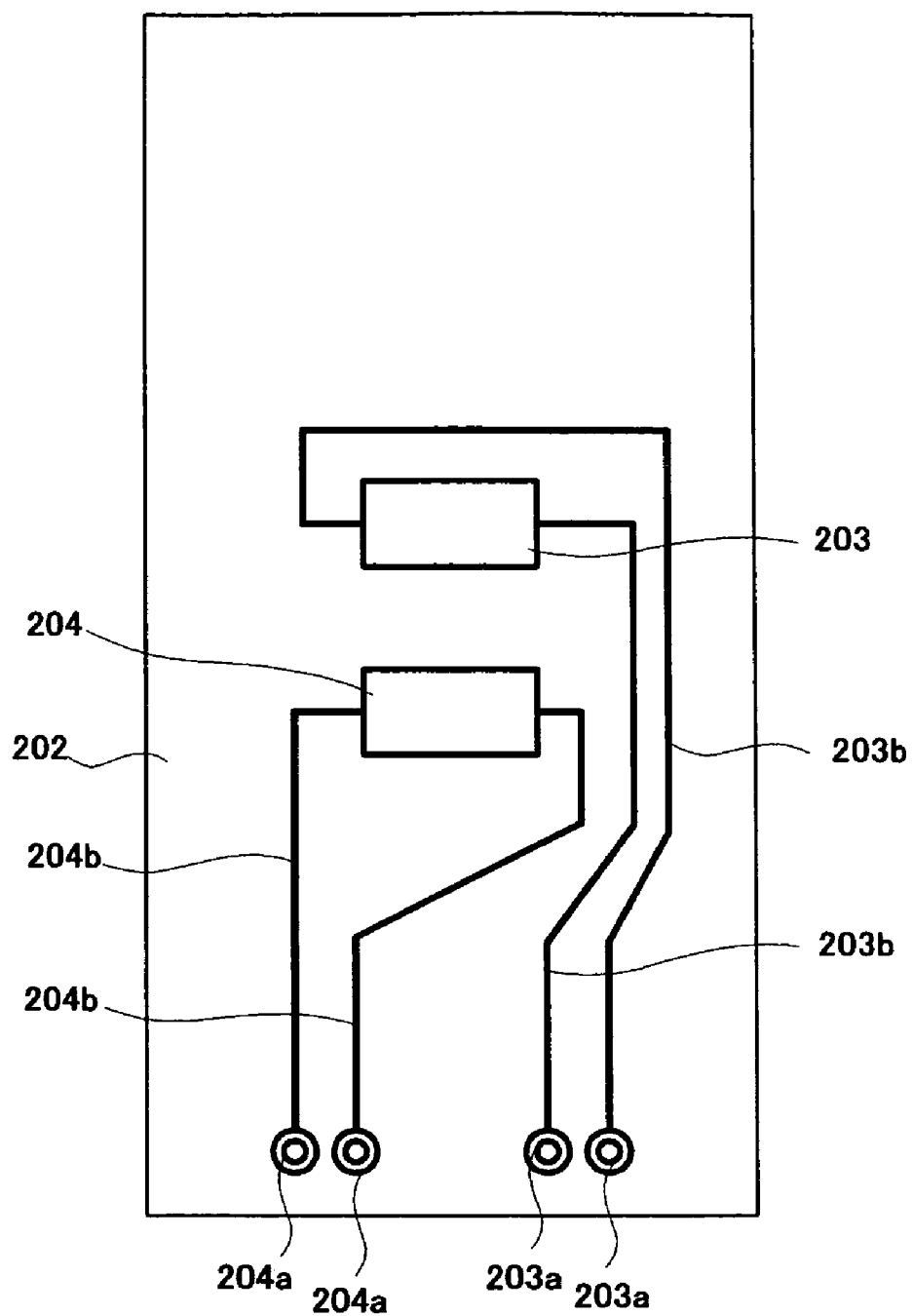
FIG. 14 shows a plan view of an example of the patterning of the heat source 203 and temperature sensor 204 in the example of FIG. 13.
Figure 15:
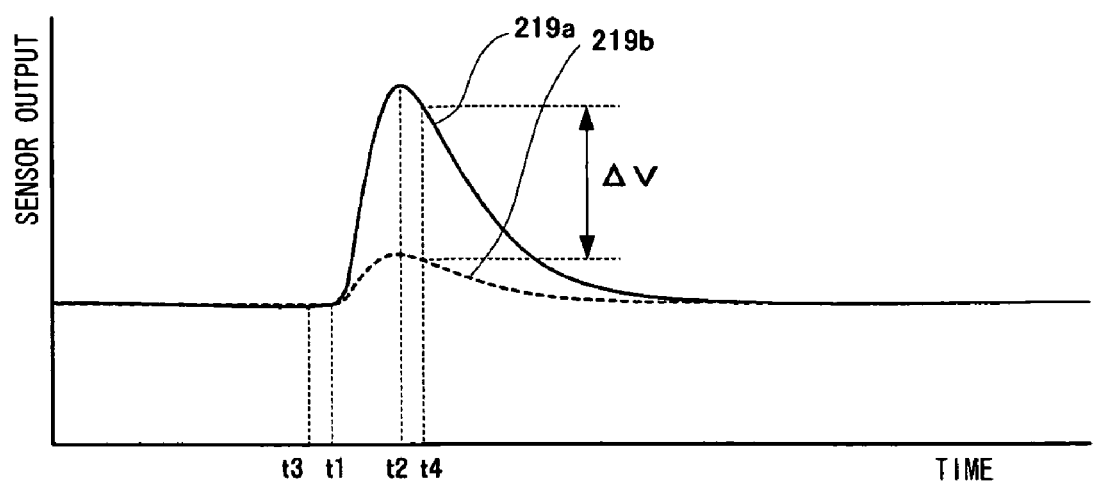
FIG. 15 shows a chart illustrating how the container surface temperature changes in the liquid determining apparatus according to Embodiment 2.
Figure 16:
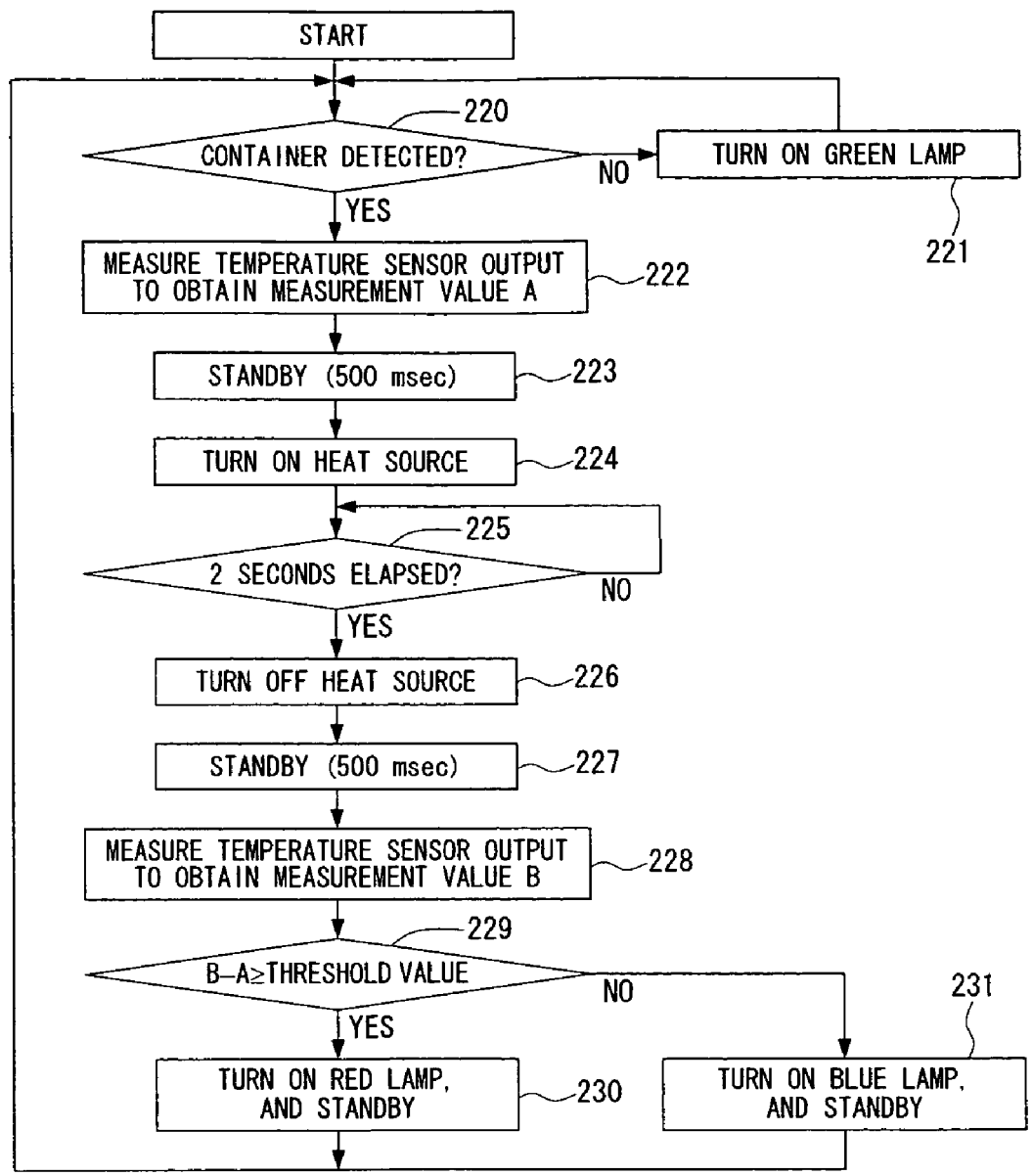
FIG. 16 shows a flowchart of an example of a method for determining the type of liquid in a container in the liquid determining apparatus according to Embodiment 2.
Figure 17:
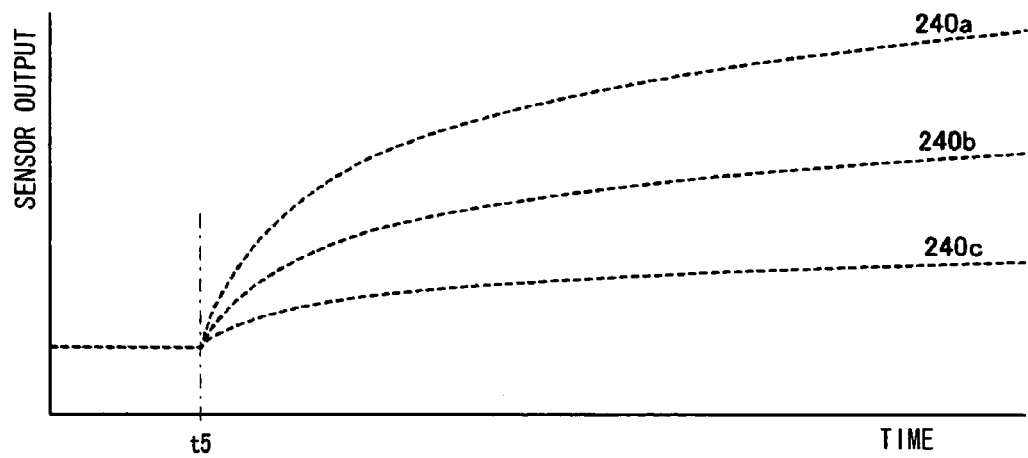
FIG. 17 shows a graph illustrating an example of the sensor output when the container temperature is different from the ambient temperature.
Figure 18:
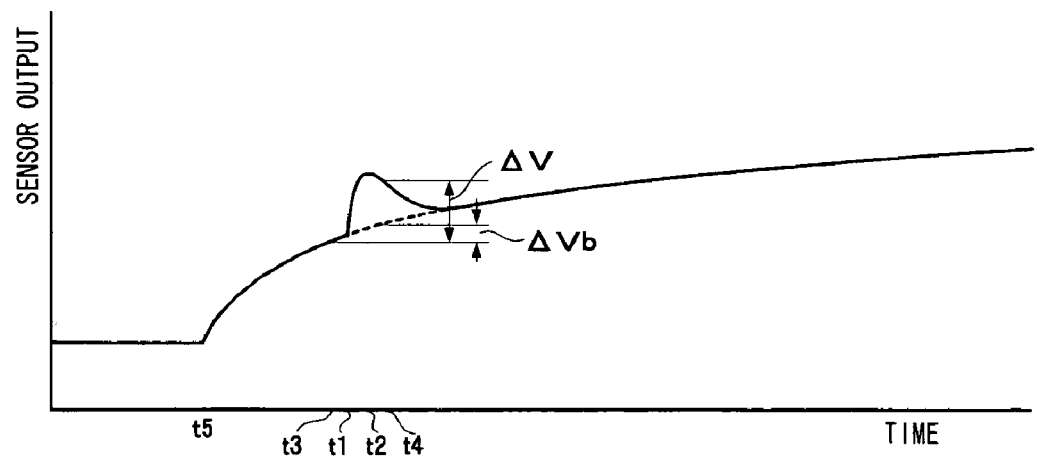
FIG. 18 shows a graph illustrating an example of the sensor output when the container temperature is different from the ambient temperature.
Figure 19:
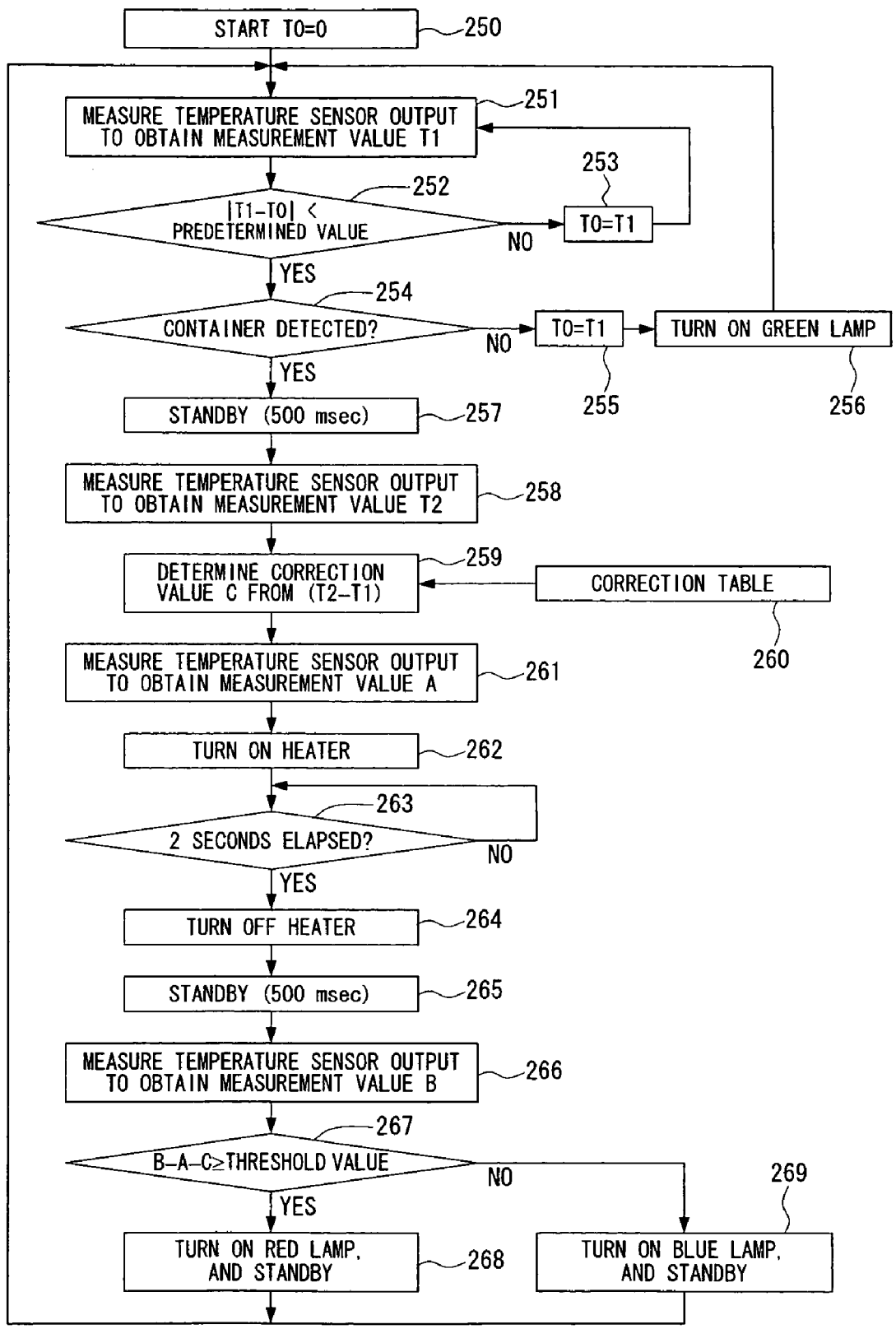
FIG. 19 shows a flowchart of an example of determination control when there is a baseline fluctuation.
Figure 20:
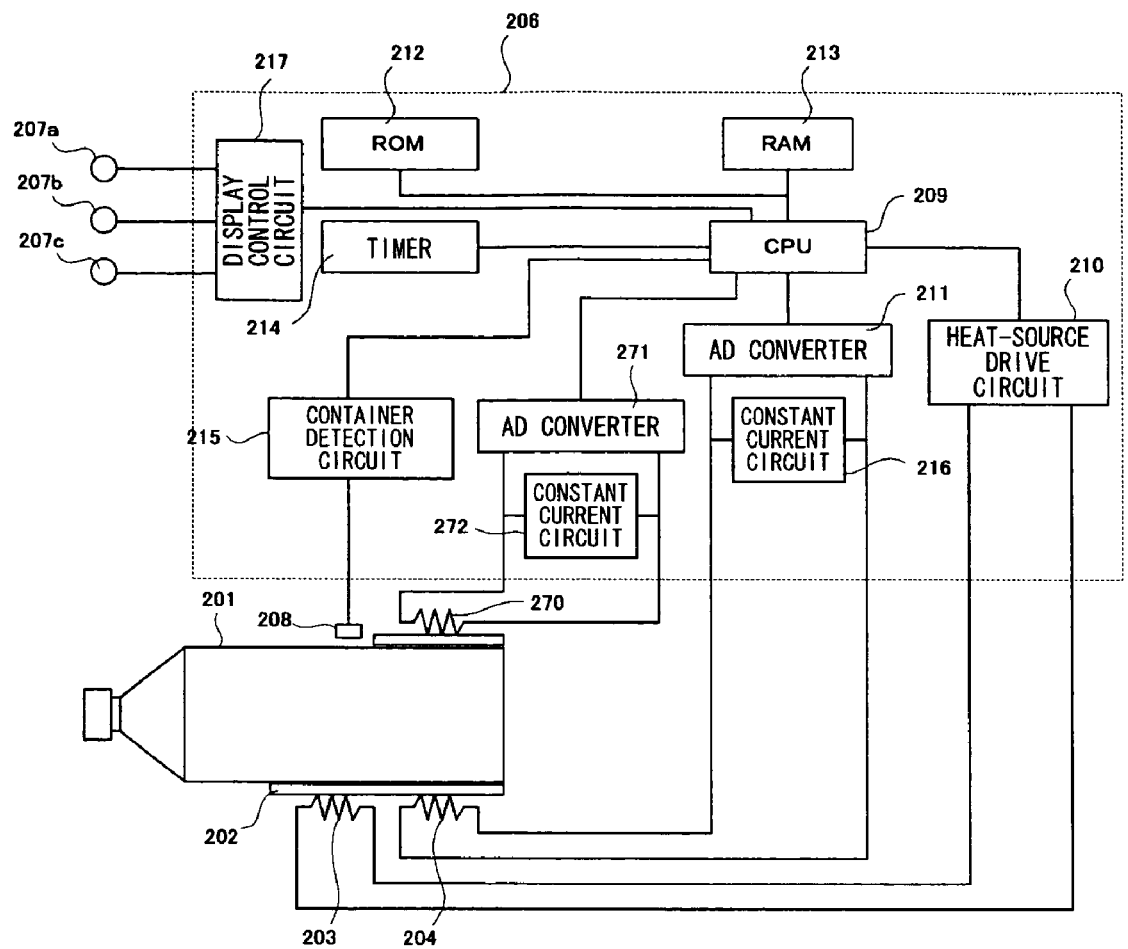
FIG. 20 shows a block diagram of another example of the structure of a liquid-type determination apparatus according to an embodiment of the invention.
Figure 21:
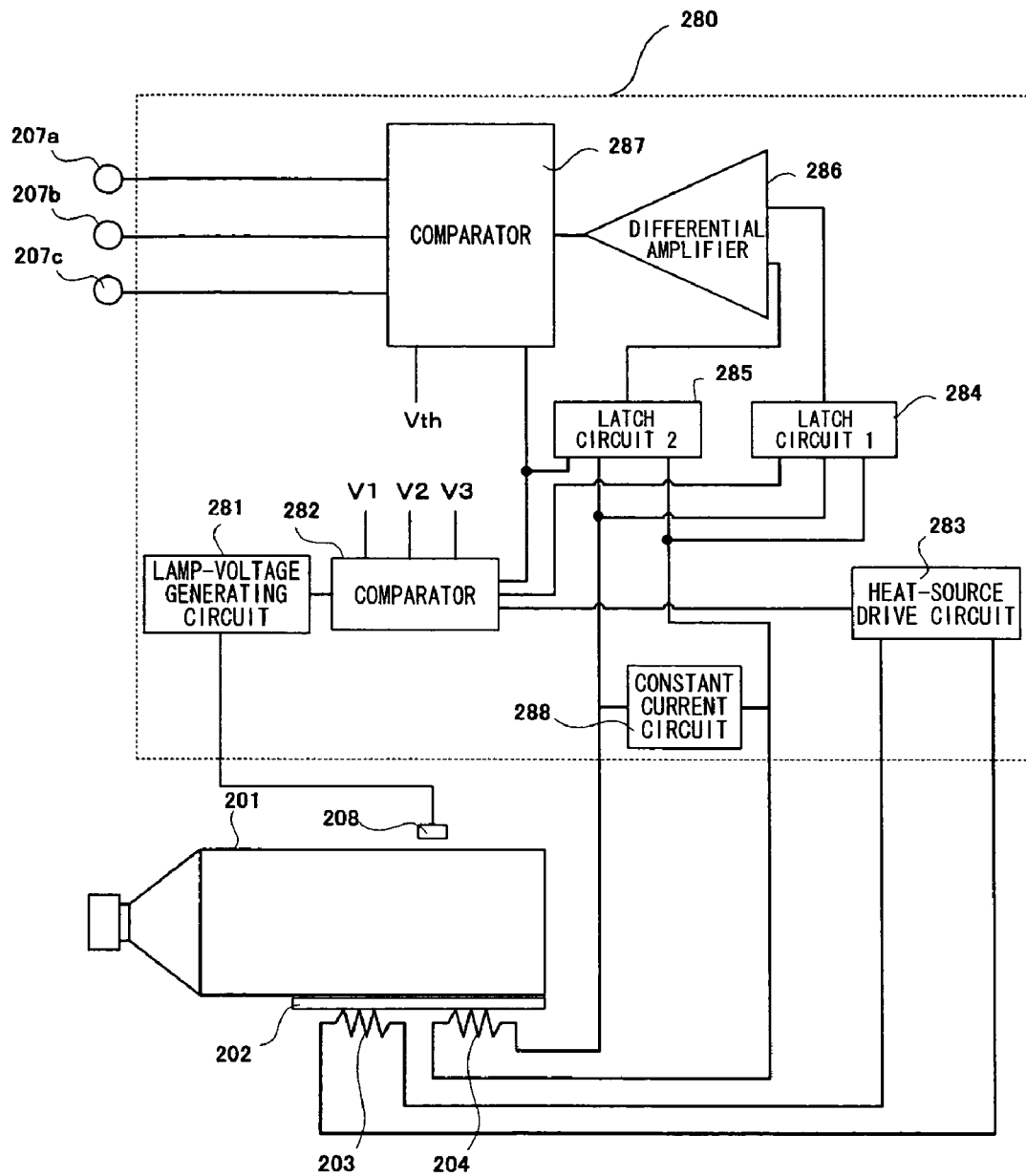
FIG. 21 shows a block diagram of another example of the structure of a liquid-type determination apparatus according to an embodiment of the invention.

101 . . . container, 102 . . . halogen heater, 103 . . . infrared thermopile, 104 . . . slit, 105 . . . heat shield plate, 106 . . . control circuit, 107a . . . LED display device, 107b . . . LED display device, 107c . . . LED display device, 108 . . . container sensor, 109 . . . CPU, 110 . . . heat-source drive circuit, 111 . . . AD converter, 112 . . . ROM, 113 . . . RAM, 114 . . . timer, 115 . . . container detection circuit, 117 . . . display control circuit, 130 . . . control circuit, 131 . . . lamp circuit, 132 . . . comparator, 133 . . . heat-source drive circuit, 134, 135 . . . latch circuit, 136 . . . differential amplifier, 137 . . . comparator, 201 . . . container, 202 . . . film, 203 . . . heat source, 204 . . . temperature sensor, 203a, 204a . . . terminals, 203b, 204b . . . wiring lines, 206 . . . control circuit, 207a, 207b, 207c . . . LED display device, 208 . . . container sensor, 209 . . . CPU, 210 . . . heat-source drive circuit, 211 . . . AD converter, 212 . . . ROM 213 . . . RAM, 214 . . . timer, 215 . . . container detection circuit, 216 . . . constant current circuit, 217 . . . display control circuit, 218 . . . container disposed portion, 218a . . . stage, 218b . . . slit, 218c . . . front plate, 260 . . . correction table, 270 . . . second temperature sensor, 271 . . . AD converter, 272 . . . constant current circuit, 280 . . . control circuit, 281 . . . lamp circuit, 282 . . . comparator, 283 . . . heat-source drive circuit, 284 . . . first latch circuit, 285 . . . second latch circuit, 286 . . . differential amplifier, 287 . . . comparator, 288 . . . constant current circuit

The invention claimed is:

1. An apparatus for determining the type of liquid in a container comprising:
a heat source disposed outside a container;
a temperature sensor disposed near said heat source for converting the temperature of an outer wall of said container into a voltage or a current;
a notification means capable of issuing an alert indicating that the content of said container is dangerous; and
a control determination circuit whereby the supply of power to said heat source is controlled, the difference between the value of an output of said temperature sensor at time t1 which is before or upon the supply of power to said heat source and the value of an output of said temperature sensor at time t1+t2, which is when a predetermined time has elapsed after said time t1, is compared with a predetermined threshold value, and an alert signal is outputted to said notification means.

2. The apparatus for determining the type of liquid in a container according to claim 1, wherein said control determination circuit comprises:
a timer;
a power supply circuit capable of supplying power to said heat source;
a notification signal generating circuit for outputting said alert signal to said notification means;
an AD converter for converting an output of said temperature sensor into digital data;
a data storage unit for recording a program and data; and
an arithmetic processing unit for carrying out processes in accordance with said program recorded in said data storage unit,
wherein said program causes said arithmetic processing unit to carry out:
a first procedure in which, on the condition that no power is being supplied from said power supply circuit to said heat source, the current time t1 is acquired from said timer, and in which data is acquired from said AD converter and recorded in said data storage unit as a value SO1;
a second procedure in which a control signal to said power supply circuit is switched to an ON signal for supplying power to said heat source, and, after a predetermined time has elapsed, the control signal is switched to an OFF signal M for supplying no power to said heat source;
a third procedure in which the current time is acquired from said timer and in which it is determined whether or not the thus acquired current time exceeds a time t1+t2 which is the sum of said time t1 and an elapsed time t2;
a fourth procedure in which, if it is determined that the current time exceeds the time t1+t2 in the third procedure, data is acquired from said AD converter and recorded in said data storage unit as a value SO2;
a fifth procedure in which the difference SO2−SO1 between said values SO1 and SO2 is calculated and compared with a predetermined threshold value; and
a sixth procedure in which said alert signal is outputted from said notification signal generating circuit depending on the result of comparison between the difference SO2−SO1 and the threshold value.

3. The apparatus for determining the type of liquid in a container according to claim 1, wherein said control determination circuit comprises:
a lamp circuit for producing a lamp voltage in response to a signal indicating the start of measurement;
a first latch circuit for latching the value of an output of said temperature sensor when the absolute value of an output of said lamp circuit is |V1|;
a power supply circuit that starts the supply of power to said heat source when the absolute value of the output of said lamp circuit is |V2| which is larger than said |V1| and terminating said supply of power after a predetermined time has elapsed;

a second latch circuit for latching the value of an output of said temperature sensor when the voltage of said lamp circuit reaches |V3| which is larger than said |V2|;

a differential amplification circuit to which the outputs of said first latch circuit and said second latch circuit are inputted; and a notification signal generating circuit for comparing an output of said differential amplification circuit with a predetermined threshold value and outputting said alert signal to said notification means.

4. The apparatus for determining the type of liquid in a container according to claim 1, wherein said heat source and said temperature sensor are disposed away from the wall of said container.

5. The apparatus for determining the type of liquid in a container according to claim 4, wherein said heat source is a halogen heater and said temperature sensor is an infrared thermopile.

6. The apparatus for determining the type of liquid in a container according to claim 5, wherein a light-absorbing heat shield member is disposed between said heat source and said temperature sensor.

7. The apparatus for determining the type of liquid in a container according to claim 1, further comprising a container sensor for detecting the placement of said container, wherein a signal from said container sensor is used as a trigger for initiating determination.

8. A method for controlling an apparatus for determining the type of liquid in a container, said apparatus comprising: a heat source disposed outside said container; a temperature sensor disposed near said heat source for converting the temperature of an outer wall of said container into a voltage or a current; a notification means capable of issuing an alert indicating that the content of said container is dangerous; and a control determination circuit, said method comprising the steps of:

storing or holding the value of an output of said temperature sensor at time t1;

starting the supply of power to said heat source at time t3 which is later than said time t1;

terminating the supply of power to said heat source at time t4 which is after said time t3;

storing or holding the value of an output of said temperature sensor at time t5 which is later than said time t3;

finding the difference between the value of an output of said temperature sensor at time t1 and the value of an output of said temperature sensor at time t5;

comparing the difference with a predetermined threshold value; and issuing an alert to said notification means depending on the result of comparison between the difference and the threshold value.

9. The control method according to claim 8, wherein said time t5 is later than said time t4.

10. The control method according to claim 8, wherein said apparatus for determining the type of liquid in a container further comprises a container sensor for detecting the placement of said container, wherein the processes after said time t1 are started using a signal from said container sensor as a trigger.

11. The control method according to claim 8, wherein said heat source and said temperature sensor are disposed away from the wall of said container.

12. The control method according to claim 11, wherein said heat source is a halogen heater and said temperature sensor is an infrared thermopile.

13. The control method according to claim 12, wherein a light-absorbing heat shield member is disposed between said heat source and said temperature sensor.

14. An apparatus for determining the type of liquid in a container comprising:

one or a plurality of flexible films in contact with a container;

a temperature sensor provided to the single film or one of said plurality of films;

a heat source provided either to the same film as or a different film from the single film or one of said plurality of films to which said temperature sensor is provided;

a notification means capable of issuing an alert indicating that the content of said container is dangerous;

a power supply means for supplying power to said heat source;

an arithmetic comparison means whereby a comparison value is calculated by acquiring an output of said temperature sensor and compared with said threshold value;

an alert signal output means for outputting an alert signal to said notification means depending on the result of comparison by said arithmetic comparison means; and a control means for controlling said power supply means, said arithmetic comparison means, and said alert signal output means.

15. The apparatus for determining the type of liquid in a container according to claim 14, wherein said film is curved and disposed such that the peak of the curvature is facing toward a plane on which said container is placed, wherein as said container is placed, said heat source and said temperature sensor are pressed against the outer wall of said container due to the flexibility of said film.

16. The apparatus for determining the type of liquid in a container according to claim 15, comprising either a first configuration in which the curved surface of said film is in contact with said container along a line in the direction of the height of said container, or a second configuration in which said curved surface is in contact with said container along a line in the circumferential direction of said container.

17. The apparatus for determining the type of liquid in a container according to claim 14, wherein said film is disposed along the outer wall of said container.

18. The apparatus for determining the type of liquid in a container according to claim 14, wherein said temperature sensor is smaller than said heat source.

19. The apparatus for determining the type of liquid in a container according to claim 14, comprising a plurality of heat sources, wherein said temperature sensor is disposed between said plurality of heat sources.

20. The apparatus for determining the type of liquid in a container according to claim 14, wherein said heat source and said temperature sensor are comprised of electric resistor elements patterned on said film.

21. The apparatus for determining the type of liquid in a container according to claim 14, wherein said control means:

controls said power supply means such that it supplies power to said heat source at time t1 and terminates the power supply at time t2 which is later than said time t1;

measures an output value O1 of said temperature sensor at time t3 and an output value O2 of said temperature sensor at time t4 which is later than said time t3 and t1; and calculates said comparison value from said output value O2 and said output value O1.

22. The apparatus for determining the type of liquid in a container according to claim 14, wherein said control means:

controls said power supply means such that it supplies power to said heat source at time t1 and terminates the power supply at time t2 which is later than t1;

measures an output value O3 of said temperature sensor at time t6 which is earlier than time t5 at which said container is placed, an output value O4 of said temperature sensor at time t7 which is later than said time t5 and earlier than said time t1, an output value O1 of said temperature sensor at time t3, and an output value O2 of said temperature sensor at time t4 which is later than said time t3 and t1;

determines a correction value from said output values O4 and O3; and calculates said comparison value from said output values O2 and O1 and said correction value.

23. The apparatus for determining the type of liquid in a container according to claim 14, wherein said control means:

controls said power supply means such that it supplies power to said heat source at time t1 and terminates the power supply at time t2 which is later than said time t1;

measures an output value O3 of said temperature sensor at time t6 which is earlier than time t5 at which said container is placed, an output value O1 of said temperature sensor at time t3, and an output value O2 of said temperature sensor at time t4 which is later than said time t3 and t1; and calculates said comparison value from said output values O2, O1, and O3.

24. The apparatus for determining the type of liquid in a container according to claim 14, further comprising a second temperature sensor disposed such that it is in contact with said container away from said heat source by a distance greater than the distance between said heat source and said temperature sensor, wherein said control means:

controls said power supply means such that it supplies power to said heat source at time t1 and terminates the power supply at time t2 which is later than said time t1;

measures an output value O1 of said temperature sensor at time t3, an output value O2 of said temperature sensor at time t4 which is later than said time t3 and time t1, and an output value O5 of said second temperature sensor at time t8 which is earlier than said time t4; and calculates said comparison value from said output values O2, O1, and O5.

25. The apparatus for determining the type of liquid in a container according to claim 24, wherein said second temperature sensor is an electric resistor element patterned on said film.

26. The apparatus for determining the type of liquid in a container according to claim 24, wherein said second temperature sensor is disposed at a position circumferentially displaced from the position where said temperature sensor and said heat source are disposed.

27. The apparatus for determining the type of liquid in a container according to claim 14, further comprising a container sensor for detecting the placement of said container, wherein determination is started using a signal from said container sensor as a trigger.

28. A method for controlling an apparatus for determining the type of liquid in a container comprising:

one or a plurality of flexible films in contact with a container;

a temperature sensor provided to the single film or one of said plurality of films;

a heat source provided either to the same film as or a different film from the single film or one of said plurality of films to which said temperature sensor is provided;

a notification means capable of issuing an alert indicating that the content of said container is dangerous;

a power supply means for supplying power to said heat source;

an arithmetic comparison means whereby a comparison value is calculated by acquiring an output of said temperature sensor and compared with said threshold value;

an alert signal output means for outputting an alert signal to said notification means depending on the result of comparison by said arithmetic comparison means; and a control means for controlling said power supply means, said arithmetic comparison means, and said alert signal output means, said method comprising the steps of:

storing or holding an output value O1 of said temperature sensor at time t3;

starting the supply of power to said heat source at time t1;

terminating the power supply to said heat source at time t2 which is later than said t1;

storing or holding an output value O2 of said temperature sensor at time t4 which is later than said time t3 and time t1;

determining said comparison value from said output values O1 and O2;

comparing said comparison value and said threshold value; and generating said alert signal depending on the result of comparison.

29. A method for controlling an apparatus for determining the type of liquid in a container comprising:

one or a plurality of flexible films in contact with a container;

a temperature sensor provided to the single film or one of said plurality of films;

a heat source provided to the same film as or a different film from the single film or one of said plurality of films to which said temperature sensor is provided;

a notification means capable of issuing an alert indicating that the content of said container is dangerous;

a power supply means for supplying power to said heat source;

an arithmetic comparison means whereby a comparison value is calculated by acquiring an output of said temperature sensor and compared with said threshold value;

an alert signal output means for outputting an alert signal to said notification means depending on the result of comparison by said arithmetic comparison means; and a control means for controlling said power supply means, said arithmetic comparison means, and said alert signal output means, said method comprising the steps of:

storing or holding an output value O3 of said temperature sensor at time t6 which is earlier than time t5 at which said container is placed;

storing or holding an output value O4 of said temperature sensor at time t7 which is later than said time t5;

storing or holding an output value O1 of said temperature sensor at time t3 which is later than said time t7;

starting the supply of power to said heat source at time t1 which is later than said time t7;

terminating the power supply to said heat source at time t2 which is later than said time t1;

storing or holding an output value O2 of said temperature sensor at time t4 which is later than said time t3 and time t1;

determining a correction value from said output values O3 and O4;

determining said comparison value from said output values O1 and O2 and said correction value;

comparing said comparison value and said threshold value; and producing said alert signal depending on the result of comparison.

30. A method for controlling an apparatus for determining the type of liquid in a container comprising:

one or a plurality of flexible films in contact with a container;

a temperature sensor provided to the single film or one of said plurality of films;

a heat source provided either to the same film as or a different film from the single film or one of said plurality of films to which said temperature sensor is provided;

a notification means capable of issuing an alert indicating that the content of said container is dangerous;

a power supply means for supplying power to said heat source;

an arithmetic comparison means whereby a comparison value is calculated by acquiring an output of said temperature sensor and compared with said threshold value;

an alert signal output means for outputting an alert signal to said notification means depending on the result of comparison by said arithmetic comparison means; and a control means for controlling said power supply means, said arithmetic comparison means, and said alert signal output means, said method comprising the steps of:

storing or holding an output value O3 of said temperature sensor at time t6 which is earlier than time t5 at which said container is placed;

storing or holding an output value O1 of said temperature sensor at time t3 which is later than said time t6;

starting the supply of power to said heat source at time t1 which is later than said time t6;

terminating the power supply to said heat source at time t2 which is later than said time t1;

storing or holding an output value O2 of said temperature sensor at time t4 which is later than said time t3 and time t1;

determining said comparison value from said output values O1, O2, and O3;

comparing said comparison value and said threshold value; and producing said alert signal depending on the result of comparison.

31. A method for controlling an apparatus for determining the type of liquid in a container comprising:

one or a plurality of flexible films in contact with a container;

a temperature sensor provided to the single film or one of said plurality of films;

a heat source provided to the same film as or a different film from the single film or one of said plurality of films to which said temperature sensor is provided;

a notification means capable of issuing an alert indicating that the content of said container is dangerous;

a power supply means for supplying power to said heat source;

an arithmetic comparison means whereby a comparison value is calculated by acquiring an output of said temperature sensor and compared with said threshold value;

an alert signal output means for outputting an alert signal to said notification means depending on the result of comparison by said arithmetic comparison means;

a control means for controlling said power supply means, said arithmetic comparison means, and said alert signal output means; and a second temperature sensor disposed in contact with said container away from said heat source by a distance larger than the distance between said heat source and said temperature sensor, said method comprising the steps of:

storing or holding an output value O1 of said temperature sensor at time t3;

staring the supply of power to said heat source at time t1;

terminating the power supply to said heat source at time t2 which is later than time t1;

storing or holding an output value O2 of said temperature sensor at time t4 which is later than said time t3 and t1;

storing or holding an output value O5 of said second temperature sensor at time t8 which is later than said time t4;

determining said comparison value from said output values O1, O2, and O5;

comparing said comparison value and said threshold value; and producing said alert signal depending on the result of comparison.

32. The method for controlling the apparatus for determining the type of liquid in a container according to claim 28, wherein said heat source and said temperature sensor are electric resistor elements patterned on said film.

33. The method for controlling the apparatus for determining the type of liquid in a container according to claim 31, wherein said heat source, said temperature sensor, and said second temperature sensor are electric resistor elements patterned on said film.

34. The method for controlling the apparatus for determining the type of liquid in a container according to claim 28, wherein said apparatus for determining the type of liquid in a container comprises a container sensor for detecting the placement of said container, wherein processes are started using a signal from said container sensor as a trigger.

* * * * *